(12) United States Patent
Shunnarah et al.

(10) Patent No.: US 11,933,671 B2
(45) Date of Patent: Mar. 19, 2024

(54) GOLD NANOPOROUS ANODIC ALUMINUM OXIDE SUBSTRATE OF AT-HOME BLOOD PHENYLALANINE MEASURING DEVICE FOR PHENYLKETONURIA AND APPLICATIONS THEREOF

(71) Applicant: MetGen, Incorporated, Atlanta, GA (US)

(72) Inventors: Richard D. Shunnarah, Atlanta, GA (US); Hugh F. Garvey, Seminole, FL (US); Lenzi J. Williams, Clearwater, FL (US); Devon Fish, Largo, FL (US)

(73) Assignee: METGEN, INCORPORATED, Atlanta, GA (US)

( * ) Notice: Subject to any disclaimer, the term of this patent is extended or adjusted under 35 U.S.C. 154(b) by 0 days.

(21) Appl. No.: 18/218,651

(22) Filed: Jul. 6, 2023

(65) Prior Publication Data
US 2023/0358609 A1    Nov. 9, 2023

Related U.S. Application Data

(63) Continuation of application No. 17/888,621, filed on Aug. 16, 2022, now Pat. No. 11,747,199.

(60) Provisional application No. 63/234,771, filed on Aug. 19, 2021.

(51) Int. Cl.
| | |
|---|---|
| *G01J 3/02* | (2006.01) |
| *G01J 3/44* | (2006.01) |
| *G01N 21/65* | (2006.01) |
| *G01N 33/52* | (2006.01) |
| *G01N 33/68* | (2006.01) |
| *G01N 3/44* | (2006.01) |

(52) U.S. Cl.
CPC .......... *G01J 3/0272* (2013.01); *G01J 3/0256* (2013.01); *G01J 3/4412* (2013.01); *G01N 21/658* (2013.01); *G01N 33/523* (2013.01); *G01N 33/6812* (2013.01)

(58) Field of Classification Search
CPC ...... G01J 3/0272; G01J 3/0256; G01J 3/4412; G01N 21/658; G01N 33/523; G01N 33/6812
USPC ..................................................... 422/82.09
See application file for complete search history.

(56) References Cited

U.S. PATENT DOCUMENTS

2007/0122867 A1* 5/2007 Shunnarah ........... G01N 33/526
                                                                                 435/27

OTHER PUBLICATIONS

Kassu, et al., Sensors 2015, 15(12), 29924-29937; https://doi.org/10.3390/s151229778. (Year: 2015).*
Li et al., AIPADVANCES, 6,125002 (2016). (Year: 2016).*
Huang, Kai & Li, Yangjuan Wu, Zhiming & Li, Cheng & Lai, Hongkai & Kang, Junyong. (2011). Asymmetric light reflectance effect in AAO on glass. Optics express. 19. 1301-9.10.1364/OE.19.001301.

(Continued)

*Primary Examiner* — Christine T Mui
(74) *Attorney, Agent, or Firm* — Locke Lord LLP; Tim Tingkang Xia, Esq.

(57) ABSTRACT

A gold nanoporous anodic aluminum oxide (NAAO) substrate used in coordination with a handheld Surface-Enhanced Raman Spectroscopy (SERS) device for detecting phenylalanine (Phe) in a sample collected from a subject, the gold NAAO substrate comprising a multilayered nanoporous aluminum layer; and a gold layer disposed on top of the multilayered nanoporous aluminum layer. The gold layer comprises gold nanoparticles.

17 Claims, 35 Drawing Sheets

(56) References Cited

OTHER PUBLICATIONS

Dengfeng Kuang, Renee Charriere, Natalia Matsapey, Manuel Flury, Jenny Faucheu, and Pierre Chavel, "Modeling the specular spectral reflectance of partially ordered alumina nanopores on an aluminum substrate," Opt. Express 23, 4506-4516 (2015).

M. Meinke, G. Muller, J. Helfmann, and M. Friebel, "Optical properties of platelets and blood plasma and their influence of the optical behavior of whole blood in the visible and near infrared wavelength range," J. Biomed. Opt., 12 014024 (2007).

Yang, Guang & Hallinan Jr, Daniel. (2016). Gold Nanoparticle Monolayers from Sequential Interfacial Ligand Exchange and Migration in a Three-Phase System. Scientific Reports.6.35339. 10.1038/srep35339.

Park, Yong-Kyun & Yoo, Sang-Hoon & Park, Sungho. (2007). Assembly of Highly Ordered Nanoparticle Monolayers at a Water/Hexane Interface. Langmuir : the ACS journal of surfaces and colloids. 23. 10505-10. 10.1021/la701445a.

Ye, Ziwei & Li, Chunchun & Chen, Qinglu & Xu, Yikai & Bell, Steven. (2021). Self-Assembly of Colloidal Nanoparticles Into 2D Arrays at Water-Oil Interfaces: Rational Construction of Stable SERS Substrates with Accessible Enhancing Surfaces and Tailored Plasmonic Response. Nanoscale. 13. 10.1039/D0NR08803J.

Yang, Guang & Chang, Wen-Sheng & Hallinan Jr, Daniel. (2015). A convenient phase transfer protocol to functionalize gold nanoparticles with short alkylamine ligands. Journal of colloid and interface science. 460. 164-172. 10.1016/j.icis.2015.08.054.

Reincke, Francois & Hickey, Stephen & Kegel, Willem & Vanmaekelbergh, Daniel. (2004). Spontaneous Assembly of a Monolayer of Charged Gold Nanocrystals at the Water/Oil Interface. Angewandte Chemie (International ed. in English). 43. 458-62. 10.1002/anie. 200352339.

Yang, Guang & Hallinan Jr, Daniel. (2016). Self-assembly of large-scale crack-free gold nanoparticle films using a drain-to-deposit strategy. Nanotechnology. 27. 225604.10.1088/0957-4484/27/22/225604.

Rohiman, Asep & Anshori, Isa & Surawijaya, Akhmadi & Idris, Irman. (2011). Study of Colloidal Gold Synthesis Using Turkevich Method. AIP Conference Proceedings. 1415. 39-42.10.1063/1. 3667215.

Mehtala, Jonathan & Zemlyanov, Dmitry & Max, Joann & Naveen, Kadasala & Zhao, Shou & Wei, Alexander. (2014). Citrate-Stabilized Gold Nanorods. Langmuir : the ACS journal of surfaces and colloids. 30. 10.1021/la5029542.

Wang, Maggie & Hoff, Alexandra & Doebler, Joseph & Emory, Steven & Bao, Ying. (2019). Dumbbell-Like Silica Coated Gold Nanorods and Their Plasmonic Properties. Langmuir. 10.1021/acs.langmuir.9b03133.14.

Saute, Benjamin & Premasiri, Ranjith & Ziegler, L. & Narayanan, Radha. (2012). Gold Nanorods as Surface Enhanced Raman Spectroscopy Substrates for Sensitive and Selective Detection of Ultra-Low Levels of Dithiocarbamate Pesticides. The Analyst. 137. 5082-7.10.1039/c2an36047k.

Md Shah, Nur & Razali, Nur & Nafisah, Suratun & Morsin, Marlia & Sanudin, Rahmat & Salleh, Muhammad. (2018). Investigation on the Effect of Centrifugation Speed on the Shape Separation of Gold Nanorods. International Journal of Engineering and Technology. 7.330-333.

Feng, Lili & Xuan, Zhenwen & Ma, Jiebing & Chen, Jun & Cui, Daxiang & su, Changwei & Guo, Junming & Zhang, Yingjie. (2013). Preparation of gold nanorods with different aspect ratio and the optical response to solution refractive index. JournalofExperimentalNanoscience.10.258267.10.1080/17458080. 2013.824619.

Al-Milaji, Karam & Zhao, Hong. (2019). New Perspective of Mitigating Coffee-Ring Effect: Interfacial Assembly. The Journal of Physical Chemistry C. 123. 10.1021/acs.jpcc.9b00797.

Yi, Johan & Jeong, Hwapyeong & Park, Jaesung. (2018). Modulation of nanoparticle separation by initial contact angle in coffee ring effect. Micro and Nano Systems Letters. 6.10.1186/s40486-018-0079-9.

\* cited by examiner

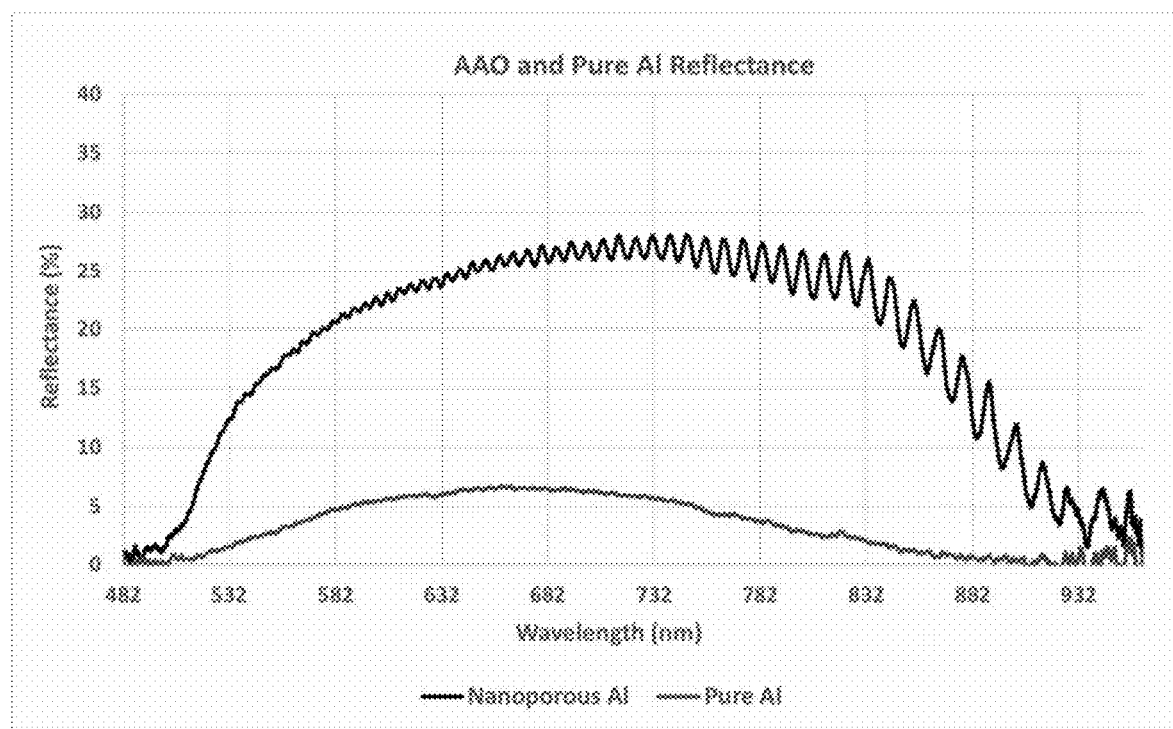
Fig. 1A
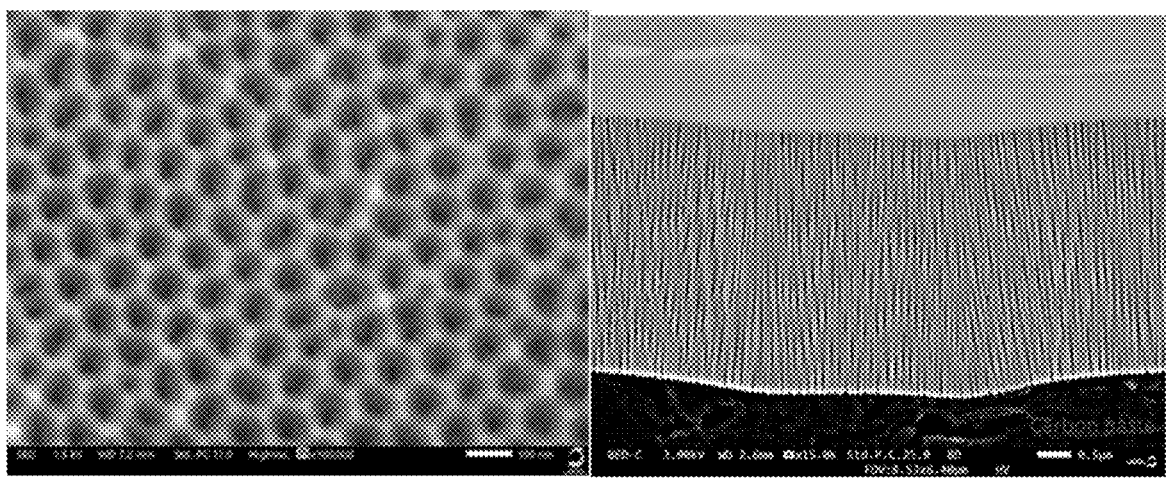
Fig. 1B
Fig. 1C

GOLD NANOPOROUS ANODIC ALUMINUM OXIDE SUBSTRATE OF AT-HOME BLOOD PHENYLALANINE MEASURING DEVICE FOR PHENYLKETONURIA AND APPLICATIONS THEREOF

CROSS-REFERENCE TO RELATED PATENT APPLICATIONS

This application is a continuation application of U.S. Non-Provisional patent application Ser. No. 17/888,621, filed on Aug. 16, 2022, which further claims priority to and the benefit of U.S. Provisional Patent Application Ser. No. 63/234,771, filed Aug. 19, 2021, both of which are incorporated herein in their entirety by reference.

FIELD OF THE INVENTION

The present disclosure relates generally to the field of biomedical engineering, and more particularly to blood phenylalanine measuring device and compatible gold nanoporous anodic aluminum oxide substrate for phenylketonuria, and applications of the same.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

Phenylketonuria (PKU) is a metabolic genetic disorder that requires lifelong specialized diets and continued blood phenylalanine (Phe) testing. Approximately 20,000 Americans live with PKU and many more people globally. The incidence rate of PKU in the United States is approximately 1:10,000 births. The incidence rate includes variants of hyperphenylalaninemia, as well. Currently, blood testing is based on age, health status, and recommended guidelines call for an average 56 tests per year per patient. The patients vary in age from newborn to adults. Regardless of age, all of the patients will need to routinely monitor blood Phe levels and undergo lifelong continuation of specialized diets. Venous blood draws are typically done at treatment centers, hospitals, clinics, doctor offices, etc. utilizing clinical labs. In addition, test results should be provided to the healthcare providers in order to reassess treatment regimens based on the most recent test findings. This is needed to adjust treatment regimens for selected foods and medications. There are approximately 115 PKU treatment centers in the United States and some states lack such care facilities. In many cases, patients travel long distances to a treatment center that involves a caregiver having to assist in the patient's needs. The ability to have a real-time blood Phe determination at one's fingertips would be a game changer for both the patient and caregiver.

For patients with PKU, adherence to treatment regimens is the major determinant to a positive health outcome. Non-compliance is detrimental to the patient since the accumulation of Phe in blood and body tissues can lead to severe intellectual impairment, neurological deficits, behavioral abnormalities, seizures and skin rashes. Although patient visits to PKU treatment centers would continue on a regular basis, the ability to have instantaneous blood test results without leaving the home would be an adjunct therapy of immeasurable impact. Thus, there is a long-felt need for at-home, real-time blood determinations for PKU, which would not only enhance the health economics of the United States, but would also advance the health and welfare of the American public.

Although rare metabolic genetic disorders exist throughout the world, the emergence of the United States as a leader in the treatment of metabolic diseases will strengthen the United States' competitiveness in global health. The improvement in quality of life, as well as reductions in time, efforts, travel and costs will truly be a health economic benefit. Similarly, people around the world would benefit from a better quality of life as well.

Therefore, there remains an imperative need for a systems/device to allow PKU patients to perform blood phenylalanine (Phe) testing at home that is capable of monitoring blood phenylalanine in a more convenient, cost effective, and with ease of operation.

SUMMARY OF THE INVENTION

In light of the foregoing, this invention discloses a novel product that would enable at-home testing of blood Phe to achieve real-time determinations. The technology of the present invention provides a miniaturized apparatus including a medical device reader and disposable parts which are used by individuals at home for testing blood Phe. The present invention incorporates Surface-enhanced Raman spectroscopy (SERS). The data shows that SERS identifies Phe in blood effectively. The present invention resolves the issue regarding the stability of the chemical interactions to identify Phe with substrates and nanoparticles. It also miniaturizes the optics needed for the measuring device. The present invention improves the in-home testing of blood Phe and provide a platform and an example of developing measuring devices for other diseases which require long-term monitoring of biomolecules.

In one aspect, the present invention provides a SERS for the accurate detection of Phe at various blood concentrations, and optimizes the miniaturization of the optics needed for the device reader. Comparing to current technologies, e.g., colorimetric test, the SERS provides a more robust test that shows reliability and accuracy. The present invention also resolves issues, including determining the proper surface chemistry, optimizing a filtering system, device miniaturization and achieving validation parameters. The present invention also improves the limit of detection for blood Phe, implements nanoparticle synthesis and NAAO fabrication protocols, and identifies specific wavelength(s).

In one aspect of the invention, the present invention provides real-time blood Phe determinations to the individual with PKU and enhances treatment regimens with respect to foods and medications. The present invention also provides platforms to be used for blood tests for related metabolic disorders, such as galactosemia and maple syrup disease, utilizing the same device platform. In particular, other diseases qualify under this device platform by reorienting the chemical interactions of the substrates and nanoparticles, with corresponding changes in wavelengths and optical designs.

In one aspect of the invention, the present invention provides real-time blood determinations, as well as transmit the latest test results to treatment centers via wireless mobile communications. The present invention circumvents constant venous blood draws because only a simple finger prick would be necessary for the present invention to determine blood Phe.

There are other metabolic disorders, such as galactosemia, maple syrup disease, homocystinuria and tyrosinemia, that can be addressed in the same manner by the platform provided by the present invention. In addition, other possible blood tests for home testing could utilize this unique technology platform, including detection of anti-cancer drugs, antibodies, cancer biomarkers, hepatitis B and illicit drugs.

The present invention comprises, among other things, an at-home blood measuring device and associated disposable blood capture chemistry strip or cassette, both are at a portable or handheld size. The SERS technology is modified and improved, and therefrom being incorporated into the Phe blood reading device with associated miniaturized optics components and disposable blood capture unit. The present invention converts a research lab benchtop SERS technology into an at-home test involving a unique chemistry system and medical device reader with miniaturized components and disposable container.

In one aspect of the invention, a gold nanoporous anodic aluminum oxide (NAAO) substrate used in coordination with a handheld Surface-Enhanced Raman Spectroscopy (SERS) device for detecting phenylalanine (Phe) in a sample collected from a subject, the gold NAAO substrate comprising a multilayered nanoporous aluminum layer; and a gold layer disposed on top of the multilayered nanoporous aluminum layer, wherein the gold layer comprises gold nanoparticles; wherein the gold NAAO substrate is configured to receive the sample; and wherein the gold NAAO substrate and the device detect the Phe in the sample.

In one embodiment, the multilayered nanoporous aluminum layer comprises an aluminum layer base, and a nanoporous alumina layer grown on top of the aluminum layer base.

In one embodiment, the nanoporous alumina layer comprises a plurality of reflective alumina nanocavities.

In one embodiment, the gold nanoparticles are nanorods.

In one embodiment, the gold nanoparticles are nanospheres.

In one embodiment, the gold NAAO substrate has a high surface area to volume ratio.

In one embodiment, the gold nanoparticles are disposed onto the multilayered nanoporous aluminum layer via a wet chemical approach.

In one embodiment, the wet chemical approach comprises injecting a cosolvent solution into a three-phase system.

In one embodiment, the three-phase system comprises air/water/hexane interfaces.

In one embodiment, the cosolvent solution comprises ethanol.

In one embodiment, the cosolvent solution is injected into the water/hexane interface of the three-phase system.

In one embodiment, the gold layer is a monolayer.

In one embodiment, the gold NAAO substrate is detachable from the device.

In one embodiment, the gold NAAO substrate is configured to receive a laser beam produced by a laser generator of the device.

In one embodiment, the laser beam reaches the sample on the NAAO and is reflected or deflected to produce a light signal; and a light sensor of the device is configured to receive the light signal reflected or deflected from the sample.

In one embodiment, the gold NAAO substrate is disposed on a test strip.

In one embodiment, the test strip is detachably received in a test strip holder of the device.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

FIG. 1A shows NAAOs were characterized by collecting the visible reflectance spectrum for the substrate before and after anodization. FIG. 1B shows SEM images of NAAOs collected using the JEOL IT700HR. FIG. 1C shows a cross-sectional view SEM image of NAAO substrate.

DETAILED DESCRIPTION OF THE INVENTION

Figure 2:
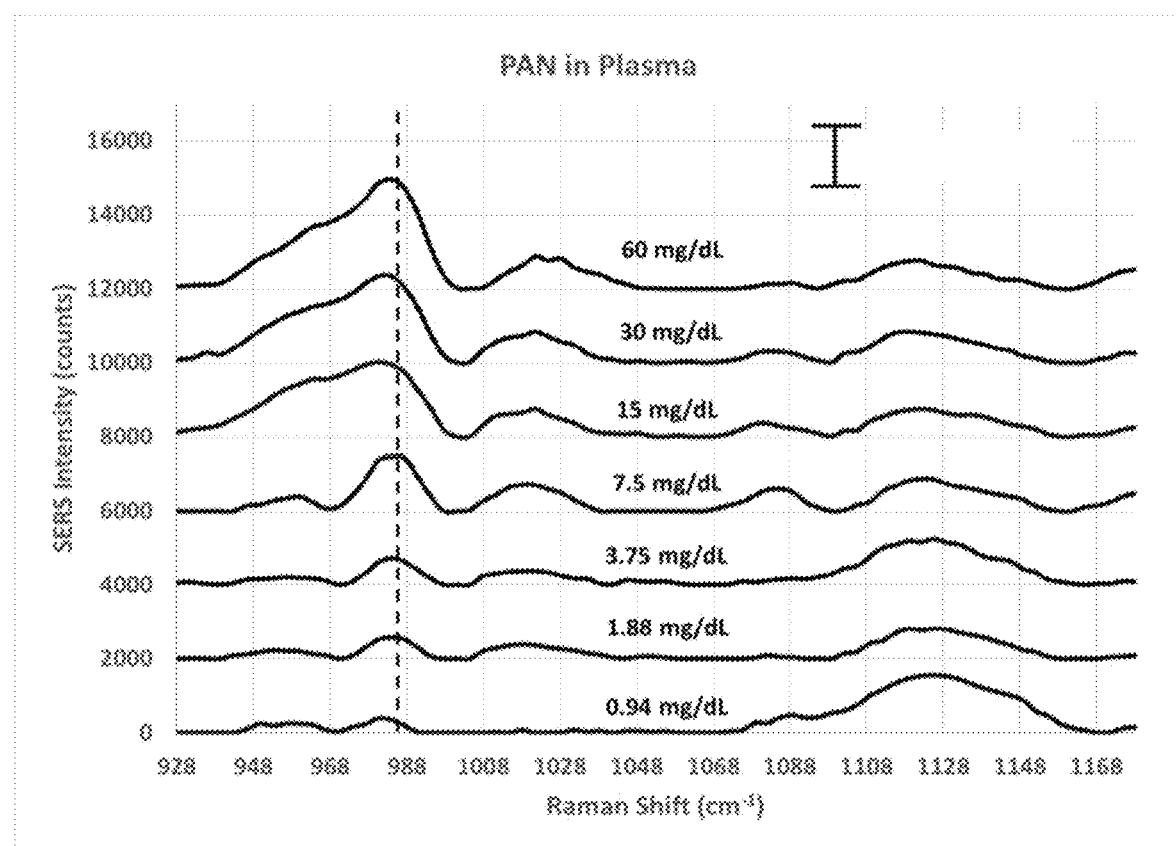
FIG. 2 shows that SERS was performed for phenylalanine in plasma at varying concentrations.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

Whenever a range is given in the specification, for example, a temperature range, a time range, or a composition or concentration range, all intermediate ranges and subranges, as well as all individual values included in the ranges given are intended to be included in the invention. It will be understood that any subranges or individual values in a range or subrange that are included in the description herein can be excluded from the claims herein.

It will be understood that, as used in the description herein and throughout the claims that follow, the meaning of "a", "an", and "the" includes plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising", or "includes" and/or "including", or "has" and/or "having", or "carry" and/or "carrying", or "contain" and/or "containing", or "involve" and/or "involving", "characterized by", and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

As used in the disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in the disclosure, the phrase "at least one of A, B, and C" should be construed to mean a logical (A or B or C), using a non-exclusive logical OR. As used herein, the term "and/or" includes any and all combinations of one or more of the associated listed items.

Present system described herein features a portable or handheld phenylalanine (Phe) measuring device coupled with highly sensitive blood testing substrates, offering a point-of-care solution for PKU patients to measure Phe concentration levels in their blood. In terms of detection of biomolecules, Raman scattering spectroscopy is cost effective and requires minimal sample preparation steps for analysis. Raman bioanalysis of whole blood requires using additional enhancement effects to improve the scattering cross-section and to reduce instrumental costs. The many advantages of Raman spectroscopy make it a promising biosensing tool, but molecular detection also depends on the sensitivity of the sample substrate and the detection optics of the spectrometer. To this end, the present invention develops and optimizes a handheld Phe measuring device based on single-point Raman detection, surface enhanced Raman scattering (SERS) spectroscopy, and disposable nanoporous anodic alumina substrates for at-home blood Phe testing.

In one embodiment, the present invention collects the SERS spectrum and measures the Phe peak intensity as a function of concentration to build a calibration curve using conventional tabletop laboratory Raman equipment. The present invention detects the Phe in plasma and in blood down to a concentration of 0.937 mg/dL and 7.5 mg/dL, respectively.

The present invention provides solutions to the following technical challenges.

I. Tailored Surface Chemistry

Success with single-point Raman highly depends on the SERS enhancement provided by the excitation properties of the nanoparticles, the interactions between Phe and the surface ligands, and the optical and mechanical properties of the nanoporous substrate. Therefore, the present invention improves the existing technologies in the following aspect:
  (1). Gain tunability in the structural parameters of the nanoparticles
  (2). Develop and implement ligand-exchange protocols, and
  (3). Fabricate alumina substrates with an optimized surface structure and pore size.

Fabricating nanoporous alumina sample substrates and determining the best sample preparation steps for SERS detection in blood is one of the major aspects of the present invention. The general scientific approach will be based on characterization of the samples using Raman spectroscopy to determine the success of the sample substrate and preparation steps.

II. Optimized Bandpass Filter System

For the proposed single-point Raman detection method, the present invention identifies the necessary bandpass filter (s) to exclusively transmit the Phe signal to the light sensor/detector. Using wavelength filtering technology, the center wavelength of each bandpass filter is controlled by tuning the angle of incidence. For collimated input light, independently rotating the bandpass filters serves to smoothly tune the combined transmission spectrum to the energy of the Phe signal. Two filters are used by the present invention to define the short- and long-wavelength edges of the overall transmission curve. Using this filter system, the device is tailored for detection of only phenylalanine and appropriate fixed filters chosen.

III. Device Miniaturization

The present invention also miniaturizes the single-point Raman spectrometer while keeping the device cost effective and easy to use. The dimensions of the laser, optoelectronics, and light sensor/detector are reduced to a compact size of the device, but remain reliable, accurate, and sensitive. The design of the present invention meets the demands of higher data acquisition and efficient power distribution.

IV. Validation Parameters

A. Selectivity: Due to spectral interference, the present invention determines the ability of the device to quantify Phe in the presence of other substances. This requires the collection of the SERS spectrum of the samples' known contributions: Phe, nanoparticles, plasma, and whole blood.

B. Limit of Detection (LOD): The LOD is determined as the lowest Phe concentration that can be distinguished from the background noise in the SERS spectrum. The LOD depends on Phe signal in plasma and whole blood.

C. Precision: A series of repeatability measurements are conducted, under the same experimental conditions, to determine a relative standard deviation for the method, the present invention determines the precision at different concentrations within the working range.

D. Working Range: The present invention determines the linear response range for Phe in plasma and whole blood. The acceptance criteria involves a Goodness of Fit test. A high correlation coefficient (r) is defined as 0.99.

E. Accuracy: The accuracy of the method should be measured against an accepted reference value or "true value". For Phe, the accuracy is defined by the comparison between this device and the clinical lab methods mentioned above.

Stability: The stability of Phe in blood-related samples is affected by the laser power density. The Phe peak intensity in the SERS spectrum can be measured as a function of time to characterize the extent of Phe stability.

In one embodiment, the handheld blood Phe measuring device of the present invention is based on surface enhanced Raman scattering spectroscopy, nanoporous anodic alumina (NAAO) test substrates, and single-point Raman detection. A single-point Raman blood measuring device would benefit the PKU community by being convenient to use, provide rapid test results, less expensive, and only requiring microliter amounts of blood for sample analysis. Innovation lies in the utilization of a dramatic enhancement effect achieved using resonant plasmonic excitation and, more importantly, metallic nanocavities for entrapping Phe and amplifying the scattered light. In fact, it is these enhancement mechanisms which make development of the single-point Raman device a viable solution for PKU patients.

The present invention discloses, among other things, the following:
(1). Design and implement nanoparticle synthesis and NAAO fabrication protocols which are tailored to the amplification of the Phe signal.
(2). Perform a proof-of-concept using a desktop Raman system and identify the limit-of-detection.
(3). Identify the specific wavelength needed to detect Phe in blood.
(4). Develop a prototype instrument that demonstrates that the technique is feasible.

Technical and commercial feasibility depends on identifying the sensitivity limits, the detectable range of concentrations, and creating an instrument at a price point that is acceptable to the marketplace.

Example 1—Detection of Phenylalanine in Blood Plasma in Handheld SERS Device

SERS-sensing using spherical gold nanoparticles (SNPs) and metalized nanoporous substrates was carried out for the trace detection of phenylalanine (Phe) dispersed in blood plasma and whole blood. The present invention incorporates fabricated nanoporous anodic aluminum oxide substrates (NAAOs). Nanoporous alumina substrates has a high surface area to volume ratio, thermal and chemical stability, and biocompatibility so as to make it a promising SERS platform. Chemistry at the self-organized and unique pore structures further enhances the SERS signal and size selection capabilities. In one embodiment of the present invention, a limit-of-detection study was performed for Phe in plasma and whole blood on NAAO substrates having an approximate 80 nm pore diameter. By incorporating this substrate, Phe can now be detected in plasma and blood to a concentration of 0.937 mg/dL and 7.5 mg/dL, respectively, without raster scanning capabilities. Improvements to the specifications of the substrate, the nanoparticle structure, and the detection parameters are also discussed.

Nanoporous Anodic Aluminum Oxide (NAAO) SERS Substrates

Anodic aluminum oxide substrates were prepared for the chemical sensing of Phe in plasma and whole blood. The NAAOs were fabricated using an electrochemical method where self-ordered nanopores growth occurs upon the anodic oxidation of pure aluminum. NAAO substrates have a high surface area to volume ratio which enhances the optical signal of Phe as it interacts with the walls of the pore channels. Additional properties of NAAOs that are important to the detection of Phe include their chemical resistance, thermal stability for increased laser power and their durability that makes for a robust substrate. NAAOs were characterized by collecting the visible reflectance spectrum for the substrate before and after anodization, as shown in FIG. 1A. The NAAOs were also characterized using scanning electron microscopy (SEM) imaging to determine the uniformity and the average pore dimensions, as shown in FIG. 1B. In addition, FIG. 1C shows a cross-sectional view SEM image of NAAO substrate.

The reflectivity of pure aluminum substrates and NAAO substrates were measured to gain insight into the success of pore formation at the surface. For the reflectance measurements, a halogen light source was guided to the aluminum surface using a visible-NIR reflectance/backscatter probe. The reflected light was collected with the same probe and delivered to a Flame spectrometer operating with a 300 µs integration time and a boxcar width of 5. To determine the ratio of reflected light to the incident light spectrum, an aluminum reflectance standard was used.

In addition to higher reflectance percentage, the spectrum for the NAAO has very clear oscillations that begin in the visible and into the NIR. The specular reflectance spectrum observed for the NAAO is attributed to the pore size and internal pore structure.

As shown in FIG. 1A, the reflectance spectrum for the porous NAAO reflects almost 20% more of the incident light than the nonporous aluminum surface. In addition to higher reflectance percentage, the spectrum for the NAAO has very clear oscillations that begin in the visible and into the NIR. The specular reflectance spectrum observed for the NAAO is attributed to the pore size and internal pore structure.

The present invention discloses that the NAAOs are a very promising SERS substrate for Phe detection in plasma. The robustness of the substrate allows higher laser powers, and the porous structure enhances the SERS signal. Using spectral reflectance analysis, one can readily identify a nanoporous surface after fabrication.

Detection of Phenylalanine in Blood Plasma on NAAOs

For the SERS measurements, the sample preparation was optimized to allow for the detection of Phe in plasma at varying concentrations (60, 30, 15, 7.5, 3.75, 1.875, and 0.937 mg/dL). To obtain a significant signal, the addition of ingredients in the SERS solution were specifically ordered. First, 20 µL of solid gold nanoparticle concentrate (SNP) was pipetted into a glass vial, followed by the careful addition of 0.6 µL 20 mM NaCl. The SNP-NaCl solution remained unmixed until right before the addition of 20 µL Phe-spiked plasma solution to the vial. Before adding the Phe-plasma solution, aggregation was confirmed by gently mixing SNP-NaCl solution until it turned greyish purple in color. The solution was gently mixed again following the addition of Phe-plasma before 5 µL was pipetted onto the substrate. Once the sample was loaded onto the NAAO, the measurement was taken immediately while the solution was still wet.

By following this sample preparation, the nanoparticles were aggregated immediately before the addition of the Phe solution which ensured molecular adsorption to the surface and hot spots of the nanoparticles. When NaCl is added and mixed after the addition of the Phe-plasma to SNP concentrate, the solution color remains dark purple, and the Phe cannot be detected.

Following specific steps for sample preparation is important to the detection of Phe in blood plasma or blood. Ensuring that the SNPs are aggregated before adding plasma increases the probability of detection. When compared to dry sampling, measuring a wet plasma/blood sample reduced the overall experimental time while maintaining the same (or greater) signal-to-noise.

As reflected in FIG. 2, SERS was performed for phenylalanine in plasma at varying concentrations. The Phe peak is located at 987 $cm^{-1}$ which is close to the ~1000 $cm^{-1}$ assignment. The intensity at 987 $cm^{-1}$ was used to detect changing levels of Phe in plasma.

As expected, the intensity of the peak increases as the concentration of phenylalanine increases. In the lower concentration range, the signal has a different spectral shape than the intensity collected at higher concentrations. The Phe peak has multiple contributions, and it is likely that a specific mode becomes less of a contribution to the overall signal at ~1000 $cm^{-1}$ as the concentration is lowered.

The position of the observed vibrational peaks is going to be influenced by the local molecular environment such as the surrounding medium and interactions amongst functional groups. The positions of spectral peaks are also sensitive to the calibration of the spectrometer and with the spectrometer Phe appears at 987 $cm^{-1}$.

Figure 3:
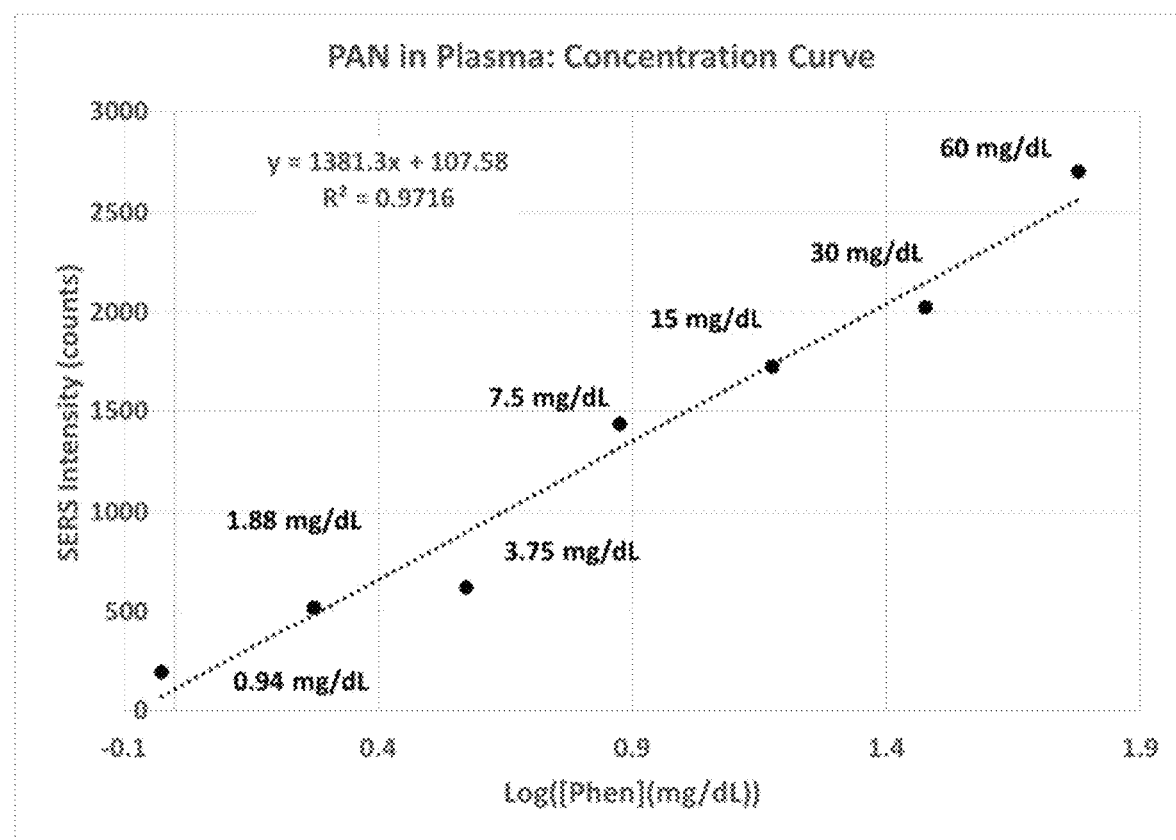
FIG. 3 shows a calibration curve was plotted to further examine detection ability of Phe-NAAOs over the concentrations 0.94 mg/dL-60 mg/dL.

In FIG. 3, a calibration curve was plotted to further examine detection ability of Phe-NAAOs over the concentrations 0.94 mg/dL-60 mg/dL. The plasma concentration range is best fit with a linear function resulting in a coefficient of determination, R2=0.9716. A limit-of-detection (LOD) was determined to be 0.94 mg/dL. For concentrations lower than 0.94 mg/dL the Phe peak did not follow the linear relationship on the calibration plot. Currently, there is no clear relationship between the SERS intensity and the low concentration range. This highlights an effect at low concentrations (<0.94 mg/dL) which may be overcome with changes in the nanoparticle structure (e.g., nanorods, spiked spheres) and the dimensions of the pores, both of which can be tailored for the Phe-NAAO system. A linear calibration curve was determined for the phenylalanine concentration range 0.94 mg/dL-60 mg/dL. Phenylalanine can be detected in plasma down to the concentration of 0.94 mg/dL. At this low concentration, a good signal-to-noise of 3 can be achieved.

Figure 4:
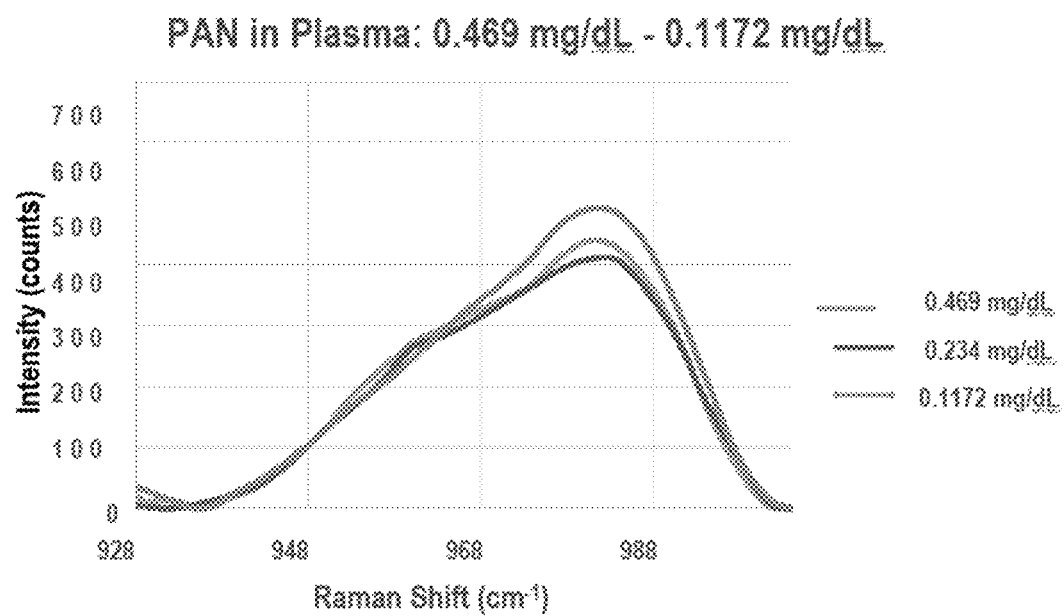
FIG. 4 depicts that SERS was performed for phenylalanine in plasma at concentrations 0.117, 0.234, and 0.469 mg/dL.

As shown in FIG. 4, SERS was performed for phenylalanine in plasma at concentrations 0.117, 0.234, and 0.469 mg/dL. For this concentration range, the Phe peak did not follow the linear relationship on the calibration plot. In this plot the lowest concentration of 0.1172 mg/dL has the highest SERS intensity. Therefore, there is no clear relationship between the SERS intensity and the above low concentration range.

Figure 5:
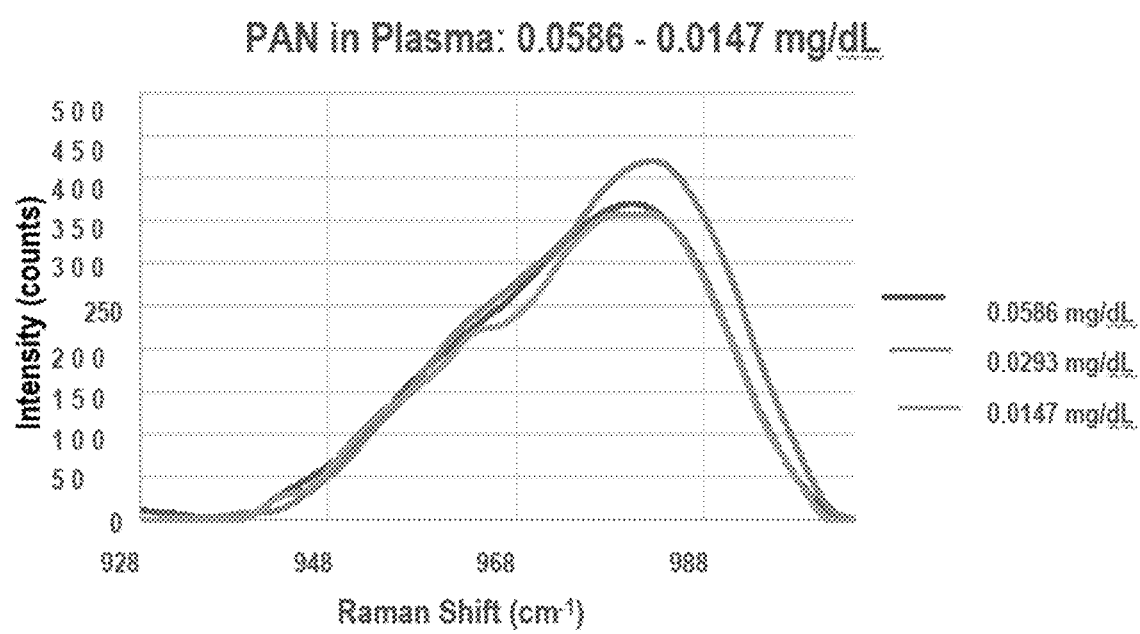
FIG. 5 depicts an effect similar to FIG. 4 occurs for the lower concentration range, 0.0586-0.0147 mg/dL.

FIG. 5 shows that a similar effect occurs for the lower concentration range, 0.0586-0.0147 mg/dL, where the Phe peak did not follow the linear relationship and there is no clear relationship between the SERS intensity and the concentration.

This highlights an effect at low concentrations (<0.94 mg/dL) which may be overcome with changes in the nanoparticle structure (e.g., nanorods, spiked spheres) and the dimensions of the pores, both of which can be tailored for the Phe-NAAO system.

Detection of Phenylalanine in Whole Blood on NAAOs

SERS measurements in whole blood requires the same sample preparation steps that were carried out for the plasma studies. Due to higher viscosities than water, blood and plasma samples require careful mixing to allow full dispersion.

Before adding the PHE-blood solution, aggregation was confirmed by gently mixing SNP-NaCl solution until it turned greyish purple in color. The solution was gently mixed again following the addition of Phe before 5 uL was pipetted onto the substrate. Once the sample was loaded onto the NAAO, the measurement was taken immediately while the solution was still wet.

It is important to properly mix the SERS solution with the patients' blood sample due to the high viscosity of blood.

Figure 6:
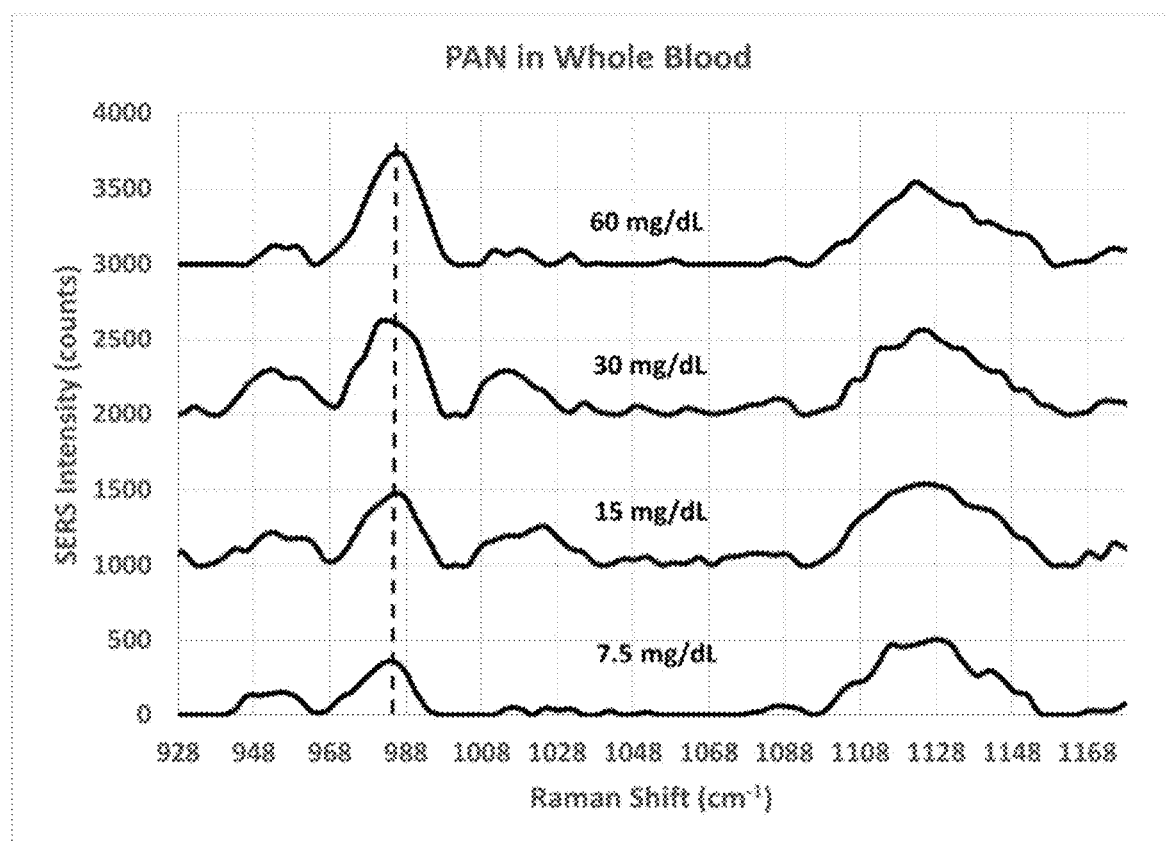
FIG. 6 depicts that SERS was performed for phenylalanine in blood at concentrations 7.5, 15, 30, and 60 mg/dL.

As shown in FIG. 6, SERS was performed for phenylalanine in blood at concentrations 7.5, 15, 30, and 60 mg/dL. Here, Phe can be detected in blood down to 7.5 mg/dL unlike the lower LOD of 0.94 mg/dL achieved in the plasma samples. The present invention attributes the different detection levels in blood to the large difference in absorption cross sections and the high refractive index of red blood cells (RBCs). The absorption and the scattering coefficient of the RBCs are two to three orders of magnitude larger than those of plasma, therefore trace detection becomes inherently more difficult. This can be overcome by further enhancing the phenylalanine Raman signal with improvements to the structures of the SNPs and the NAAOs.

Figure 7:
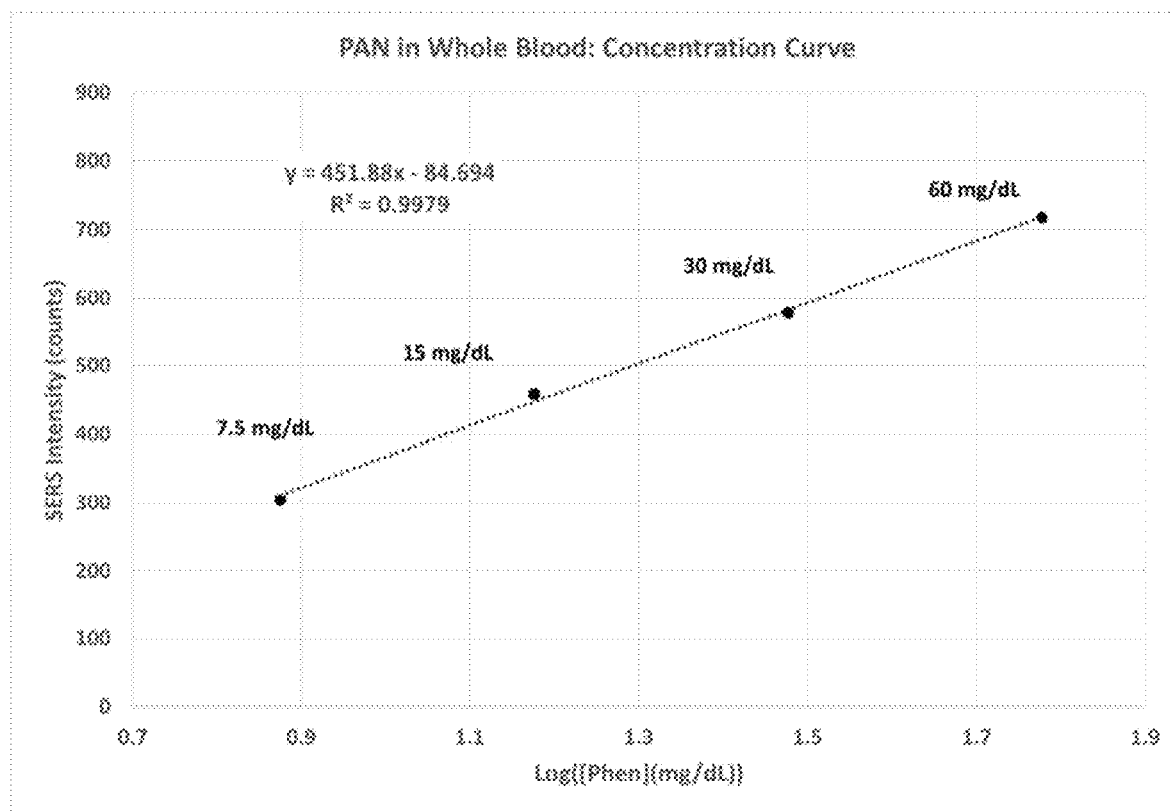
FIG. 7 shows that the calibration curve was obtained by plotting the SERS peak intensity at 987 cm-1 as a function of the logarithmic concentration of Phe.

According to FIG. 7, the blood concentration range is best fit with a linear function resulting in a coefficient of determination, R2=0.9979. A linear calibration curve was determined for phenylalanine in blood over the concentration range 7.5 mg/dL-60 mg/dL. Phe is detected in blood down to a concentration of 7.5 mg/dL, unlike the lower concentration detected in plasma. SERS spectra were also collected for Phe at concentrations 0.469, 0.937, 1.785, and 3.75 mg/dL. The 7.5 mg/dL sample shares a similar SERS response with the 3.75 mg/dL sample despite having a higher concentration. The similar SERS response is also shared by the 1.875 mg/dL sample and the 0.937 mg/dL sample, where the signals are comparable but with the lower concentration having a slightly higher intensity. The sample with the lowest concentration is almost double the counts collected for the 7.5 mg/dL sample.

Figure 8:
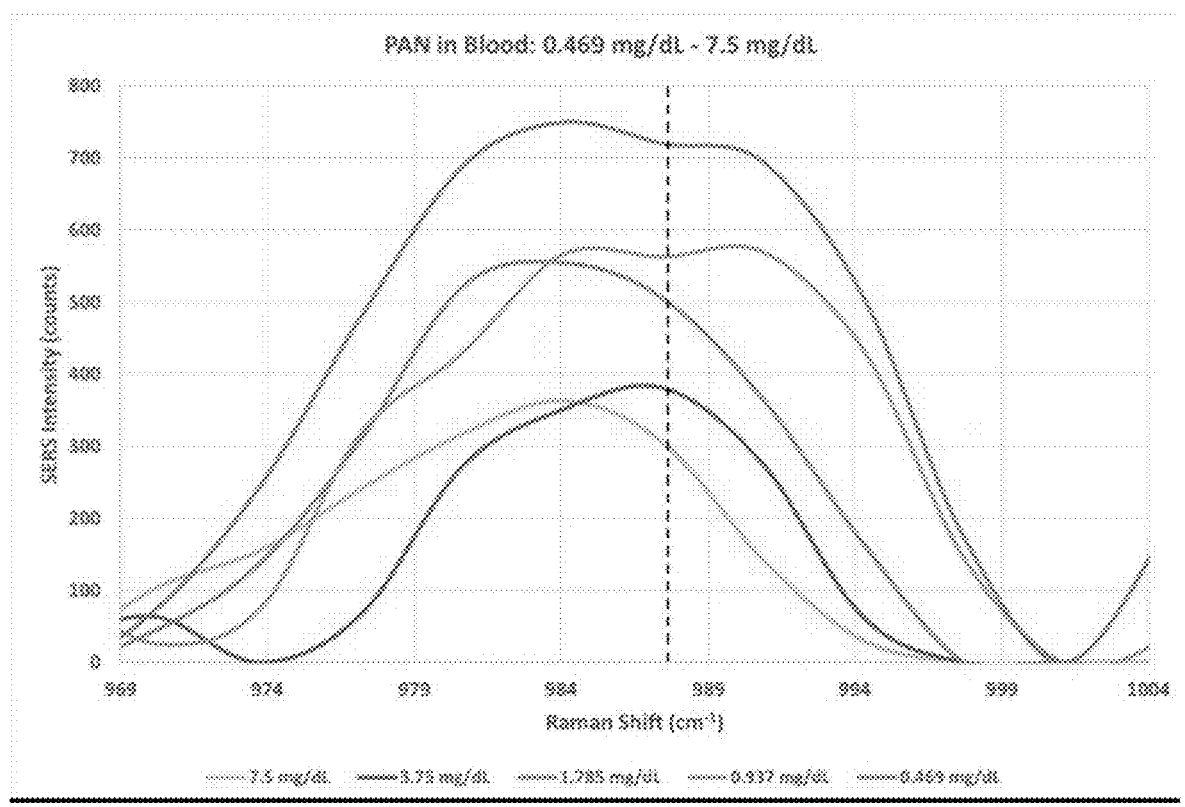
FIG. 8 shows that the SERS spectra were also collected for Phe at concentrations 0.469, 0.937, 1.785, and 3.75 mg/dL.

According to FIG. 8, SERS spectra were also collected for Phe at concentrations 0.469, 0.937, 1.785, and 3.75 mg/dL. The 7.5 mg/dL sample shares a similar SERS response with the 3.75 mg/dL sample despite having a higher concentration. This is also the case for the 1.875 mg/dL sample and the 0.937 mg/dL sample, where the signals are comparable but with the lower concentration having a slightly higher intensity. The sample with the lowest concentration is almost double the counts collected for the 7.5 mg/dL sample. The intensity at 987 $cm^{-1}$ was closely monitored by measuring the peak intensity with respect to the concentration and plotting these values.

Figure 9:
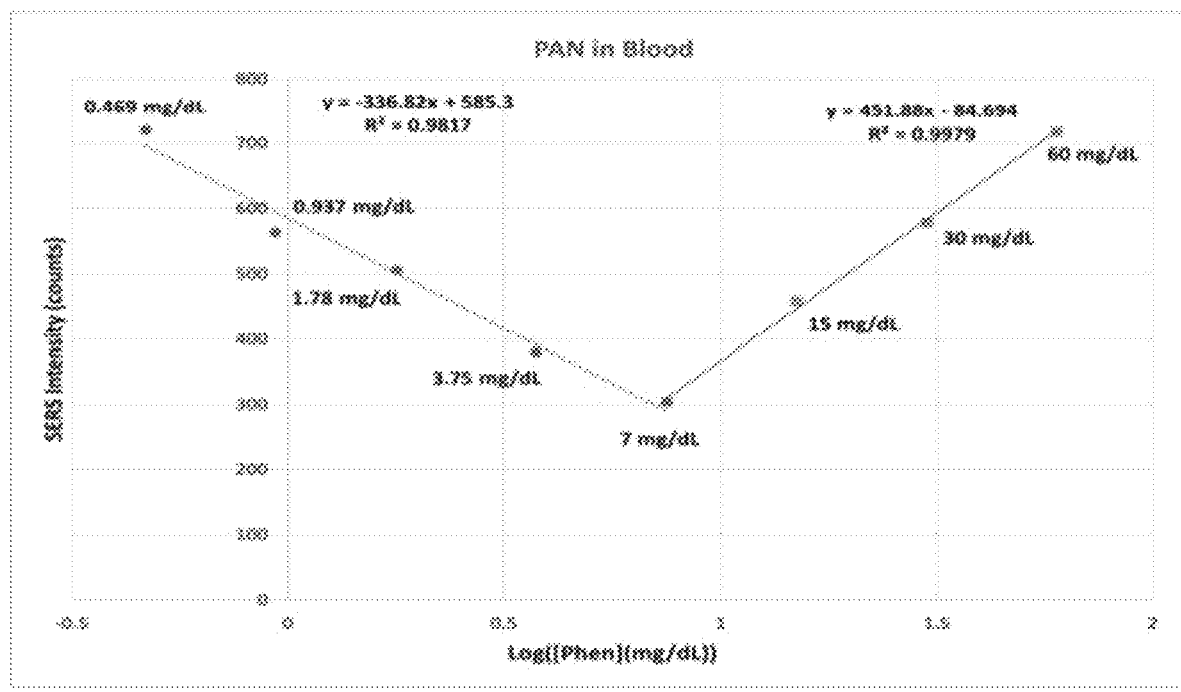
FIG. 9 shows that, in the SERS intensity of Phe in blood, the peak intensities at lower concentrations (blue circles) do not follow the same trend as the higher concentration samples orange squares).

According to FIG. 9, the intensity at 987 $cm^{-1}$ was closely monitored by measuring the peak intensity with respect to the concentration and plotting these values. The peak intensities at lower concentrations (blue circles) do not follow the same trend as the higher concentration samples (orange squares). In fact, the SERS intensity linearly increases with decreasing concentrations. When a linear fit is applied to the lower concentration regime, a systematic effect is occurring. This effect at low concentrations of Phe is likely due to changes in the Phe adsorption coverage on the nanoparticle. The increase is likely due to another mode, such as phenylalanine isomer, tyrosine, that is prone to build up in this concentration range and with the current collection parameters. To uncover and separate these two effects in blood, the Phe signal needs further enhancement. The collection parameters and laser power can also be optimized to detect Phe in blood under 7.5 mg/dL. In addition to instrumental changes, the structure of the nanoparticle can also aid in furthering the enhancement. Along with the spherical nanoparticles, gold nanorods were prepared and substituted in this system to aid with Phe detection.

In the present invention, all of the measurements made to date were done using a conventional desk-top Raman system, which is effective but costly. To make a cost-effective solution, the instrumentation must be simplified considerably.

As already demonstrated in FIGS. 2 and 6, the signal from phenylalanine predominantly affects only a small portion of the Raman spectrum. Therefore, rather than collecting the whole Raman spectrum each time, with the associated complex instrumentation required for such a measurement, in one embodiment, the present invention focuses on the exact part of the spectrum associated with the phenylalanine signal and collects only the signal generated at that wavelength or potentially group of wavelengths and completely disregarding the rest of the spectrum. It then becomes possible to dramatically simplify the instrumentation eliminating the need for a grating and an area detector in favor of some simple filters, lenses and a low-cost single photodiode detector.

Early tests have demonstrated that the best results were obtained by scanning the laser over a larger area of the sample, which again is not possible in a simple handheld instrument due to cost considerations. The present invention, in one embodiment, uses a cylinder lens as the focusing lens to create a line rather than a spot covering a larger area of the sample. This may however reduce the power of the laser at any given point enough to have a counterproductive effect. The present invention establishes a functional model of this approach, as well as optimizing the laser line width and length. The optimization of the sample signal using the improved substrate detailed above is also instrumental to making this approach possible.

Figure 10:
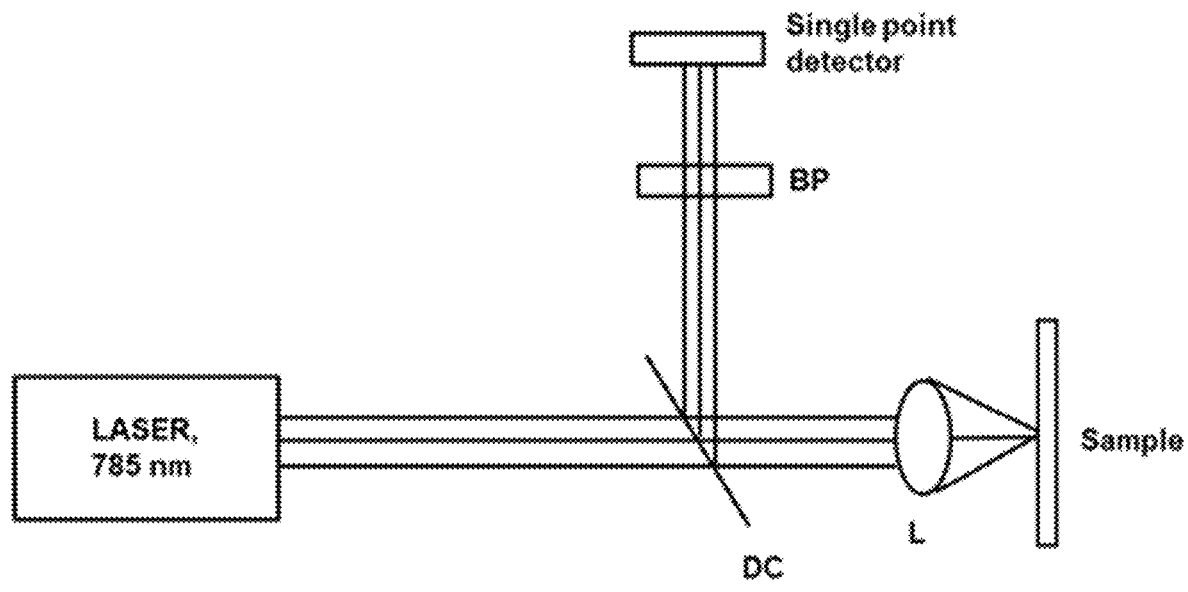
FIG. 10 shows single-point Raman initial test schematics.
Figure 10:
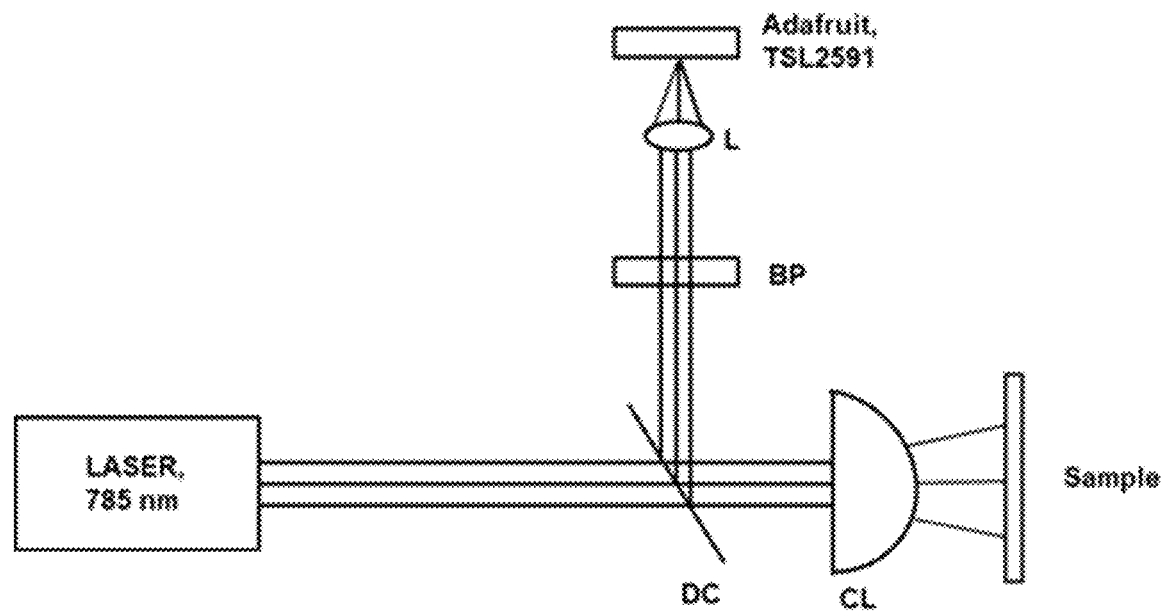

To aid in the development of the final system, a more complicated alternative system has been developed. As shown in FIG. 10, by using two variable bandpass filters to create a narrow, but moveable signal window as tests are done to home in on the exact wavelength(s) required for optimal phenylalanine concentration detection. Once the optimal wavelength(s) is determined, the variable filters can be replaced with fixed narrowband pass filters as mentioned above.

In one illustrative embodiment, CTAB-NRs were prepared using a seeded-growth method. NIR plasmon peak generated at 800 nm ($\lambda exc$=785 nm). Ligand exchange is required for successful Phe surface adsorption, Cit-GNRs. Centrifugation, separation and redispersion steps are being optimized for concentrate formation.

In one illustrative embodiment, Nanoparticle sensing solution is used for nanoparticle concentrate-coated NAAO. For Au NP concentrate, colloidal solution is centrifuged and separated, while for Au NP Sensing solution, there is no NaCl activation agent, less sample preparation steps. Also, there is no mixing, and the samples are directly loaded onto NAAO. Therefore, the time of measurement is reduced.

In one illustrative embodiment, the present invention discloses NIR Excitation Mode with Spherical NPs. Reflectance spectrum for SERS-NAAOs using spherical particles present absorption modes* at ~500 nm and ~900 nm. Similarly, to the nanorods absorption spectrum, spherical nanoparticles loaded onto NAAOs generate a NIR band. Spherical nanoparticles of different sizes are being tested with this method.

In one illustrative embodiment, the present invention discloses NAAO fabrication and characterization. Phenylalanine is at 60 mg/dL in water 120 mW, 5 s is used for integration. Phe signal intensity on SERS-NAAO can be ~2× that of the SERS solution. However, deposition coverage is inconsistent from chip to chip.

Example 2—Fabrication of NAAO Substrate and Test Strip

The present invention is also directed to a centimeter-scaled, gold-layered SERS-NAAO substrate scalable fabrication process based on the air-water-oil interfacial self-assembly of gold nanoparticles (NPs) into 2D arrays at the surface of a nanoporous alumina layer. It is an objective of the present invention to provide a cost-effective SERS substrate fabrication for the Raman enhanced detection of phenylalanine by combining gold nanoparticle colloidal solutions and non-lithographic (wet-chemical) protocols for preparing reflective alumina nanopores. An appropriate combination of surface structure, nanostructure morphology, and physical and chemical properties were determined for phenylalanine sensing.

The air-water-oil assembled gold nanoparticles provided localized electric fields at the interparticle gaps ("hot spots) of the nanoparticles. The concentrated electric fields would provide the enhancement to the Raman signal of phenylalanine. The alkylamine ligand implemented for the self-assembly and the size of the nanoparticles greatly contributed to the localized field, therefore also the nanoparticle-adsorbed phenylalanine Raman enhancement.

An alumina substrate surface was chosen as a promising platform for gold layering. The binding of the gold NPs onto the surface depends largely on the surface species provided by alumina. Therefore, great care has been taken in choosing a simple gold assembly method where an alkylamine-functionalized nanoparticle has favorable interactions with the hydroxyl groups at the surface of alumina. Here, strict fabrication parameters were created to form ordered nanopores, to induce an efficient in-situ ligand exchange, to create a uniform gold layer, and to preserve the integrity of the gold layer after drying, and to promote phenylalanine surface adsorption.

An ordered nanoporous alumina layer is grown atop an aluminum substrate using a scalable wet-chemical two-step anodization process. Before gold layering, the resulting NAAO structure is multilayered, $Al_2O_3/Al$.

An air-water-oil in-situ alkylamine ligand exchange, induced by a reduction in electrostatic repulsive forces, drives the self-assembly of negatively charged citrate-capped spherical NPs (~60 nm diameter). Under the same experimental parameters as the spherical morphology, positively charged CTAB-capped nanorods did not form long-range gold layers across the centimeter scale square substrate.

An efficient self-assembly of the gold NPs and detection of phenylalanine in blood was promoted by (a) concentrated aqueous spherical gold nanoparticles (~60 nm diameter) layer, (b) micromolar concentration of the alkylamine-hexane organic layer, (c) partially controlled air phase within a triple vented, lidded polystyrene container, (d) slow evaporative drying at room temperature.

Figure 35:
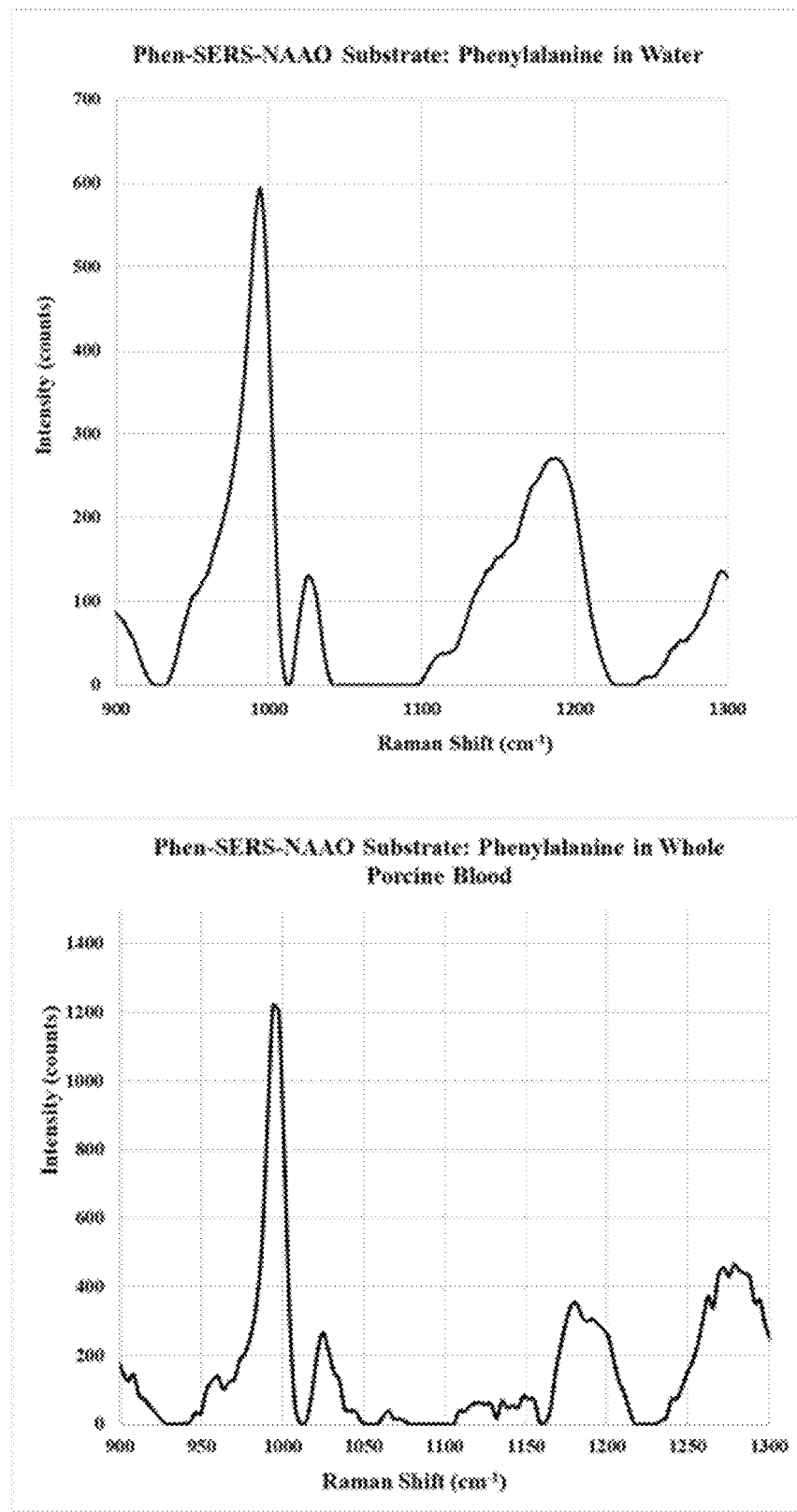
FIG. 35 upper panel shows SERS spectrum of phenylalanine in water adsorbed to the SERS-NAAO substrate, and the lower panel shows SERS spectrum of phenylalanine in whole porcine blood adsorbed onto the SERS-NAAO substrate.

FIG. 35 upper panel shows SERS spectrum of phenylalanine in water adsorbed to the SERS-NAAO substrate, and the lower panel shows SERS spectrum of phenylalanine in whole porcine blood adsorbed onto the SERS-NAAO substrate.

The Phe SERS sensing on nanoporous anodic aluminum oxide (NAAO) substrates used a mixed sample-nanoparticle test solution, which was deposited onto NAAO substrates before taking the measurement. Using this premixing procedure, a limit of detection (LOD) of Phe in plasma and blood was determined to be 0.94 mg/dL and 7.5 mg/dL, respectively. For at-home detection, a significant issue with this method is that the premixing introduces additional steps for the user, which could complicate testing and obscure the results. To confront this matter, the present invention discloses another embodiment, which discloses a low-cost, wet chemical, and scalable water/oil/air three-phase (tp) ligand exchange approach for gold layering the NAAO substrates. This approach is a thermodynamically controlled process in which a cosolvent induces the ligand exchange, phase transfer, and the self-assembly of the gold nanoparticles. The nanoparticles which were formally dispersed in the sample nanoparticle-test solution, now with the three-phase protocol, have a different ligand which promotes film formation. In this way, the premixing steps are eliminated, and the user can deposit their sample directly onto the gold-coated substrate before taking the measurement.

In one embodiment, the present invention uses a water/oil/air three-phase gold layering protocol to prepare SERS-active NAAO substrates. Fabrication steps are disclosed to highlight the synthetic parameters which must be controlled for layer formation. Qualitative data, such as videos and optical images provide first insights into the assembly of the gold nanoparticles before and after drying. Additionally, the surface optical properties of the gold coated NAAO were characterized using reflectance spectroscopy. The reflectance spectra provided insight into the coupling of the gold nanoparticles deposited at the surface and the resulting localized surface plasmon resonance (LSPR) wavelength for SERS excitation. The chemical sensing capability of the resulting three-phase SERS NAAOs were also investigated by collecting the SERS signal of the classic test molecule, Rhodamine 6G, following 785 nm excitation.

Ultimately, the SERS signal for 250 mg/dL phenylalanine in water and whole blood loaded onto a SERS-NAAO substrate were measured. The present invention shows an appreciable SERS signal when Phe was loaded onto the gold layered NAAO substrate. This was confirmation that the self-assembled nanoparticles, despite undergoing a ligand exchange to self-assemble, provided concentrated electromagnetic fields for the SERS sensing of phenylalanine. SERS experiments were conducted at multiple points across a 10×10 mm substrate to determine an overall signal uniformity error of ~20% for the current fabrication protocol.

Fabrication of SERS-NAAO Substrates: Three-Phase Gold Layering

Fabrication of SERS-NAAO substrates is based on a low-cost wet chemical approach to develop gold layers directly onto substrates. A three-phase system comprised of air/water/hexane interfaces promotes the self-assembly and migration of gold nanoparticles into a two-dimensional thin film structure upon the addition of a cosolvent. The formation mechanism involves injecting ethanol at the water/hexane interface, which induces the gold nanoparticles to diffuse to this interface where an in-situ ligand exchange passivation temporarily traps the nanoparticles. Next, the ligand-exchanged nanoparticles migrate to the air/water interface, where they self-assemble to form a gold monolayer on top of the NAAO substrate. The new ligand helps reduce the electrostatic repulsion, by controlling the interparticle separation between the nanoparticles, therefore causing the formation of gold layer.

First, for a laser-cut 10×10 mm (4×4, 5×5, and 7×7 mm SERS-NAAO available) NAAO substrate, the aqueous nanoparticle layer was established by pipetting 80 µL of the concentrate onto a single NAAO substrate which was placed in a disposable petri dish. If more than one substrate was processed in the same dish, they were sufficiently separated to prevent interfering layer formation. After depositing the concentrate, milliliter amounts of a long-chain amine doped hexane (uM) solution were slowly added to the petri dish to submerge a portion of the concentrate droplet, but allow the droplet to protrude forming an air/water/hexane interface. As shown in FIG. 11A-E, using a sterile syringe, microliter amounts of ethanol were injected (1 drop/min) at the water/hexane interface to induce gold layer formation. The wet substrates dried overnight before use in SERS measurements.

Figure 11A:
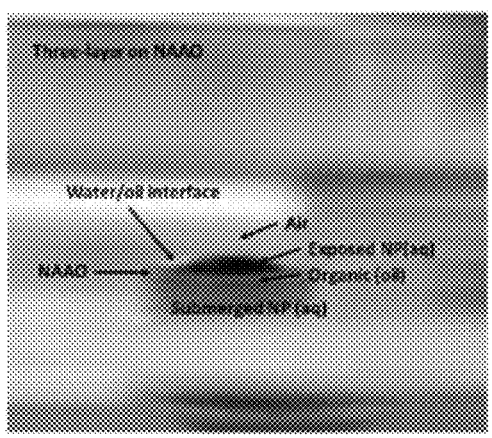
FIG. 11A shows lateral side of a three-phase assembly atop an individual NAAO in a plastic petri dish.
Figure 11B:
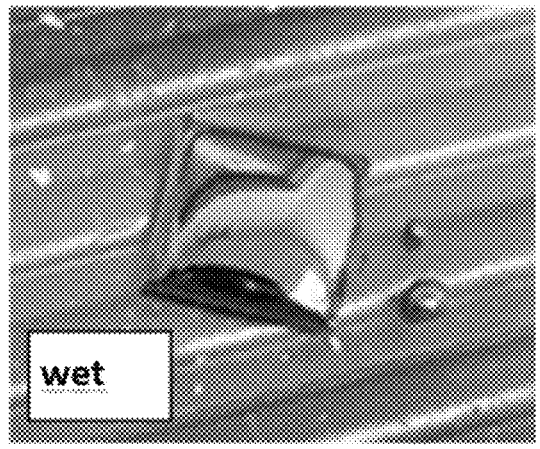
FIG. 11B shows a top view of wet assembled gold NP layer atop NAAO.
Figure 11C:
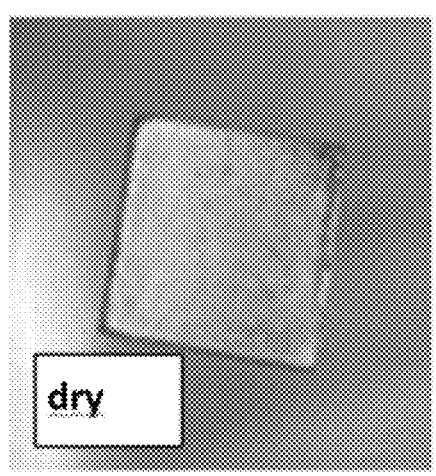
FIG. 11C shows a top view of NAAO after overnight drying.
Figure 11D:
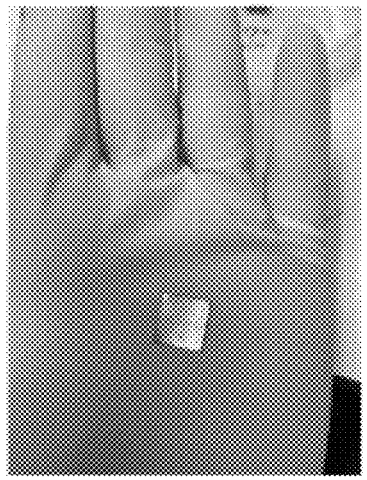
FIG. 11D shows the size of 10×10 mm SERS-NAAO relative to a human hand.
Figure 11E:
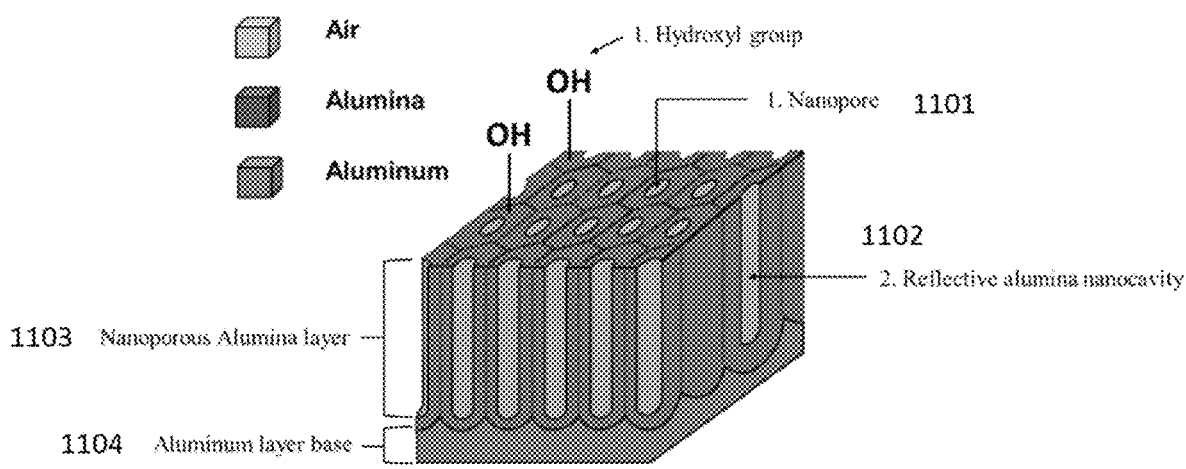
FIG. 11E shows a diagram of nanoporous anodic aluminum oxide substrate layers.

FIG. 11A shows lateral side of a three-phase assembly atop an individual NAAO in a plastic petri dish. FIG. 11B shows a top view of wet assembled gold NP layer atop NAAO, and FIG. 11C shows a top view of NAAO after overnight drying. FIG. 11D shows the size of 10×10 mm SERS-NAAO relative to a human hand. FIG. 11E shows a diagram of nanoporous anodic aluminum oxide substrate layers. In particular, the substrate has a nanoporous alumina layer 1103 laid on top of an aluminum layer base 1104. Within the nanoporous alumina layer 1103, there are arrays of nanopores 1101 providing reflective alumina nanocavity 1102.

The present invention explored different drying methods, including oven, heat gun, freezer, microwave, and cool fan, to efficiently dry the gold-coat after development. The chosen drying method had to leave the assembled film undisturbed and preserve the optical properties (reflectance) of the nanoparticles after drying. Overnight drying at room temperature is the often-used method for evaporating solvents and allowing the film to dry with extended time. This overnight drying method has proven to be the most effective for drying the SERS-NAAO. Additional studies were also carried out to reduce the drying time. For example, setting the substrates near a fume hood where air is being flushed out of the hood decreases the drying time.

Key points for fabrication process includes (1) NAAO substrates can be laser cut to various shapes and sizes; (2) gold layering is due to an in-situ ligand exchange; (3) only using overnight drying; (4) air venting being explored for faster drying.

Aqueous Phase: Gold Nanostructures

Figure 12:
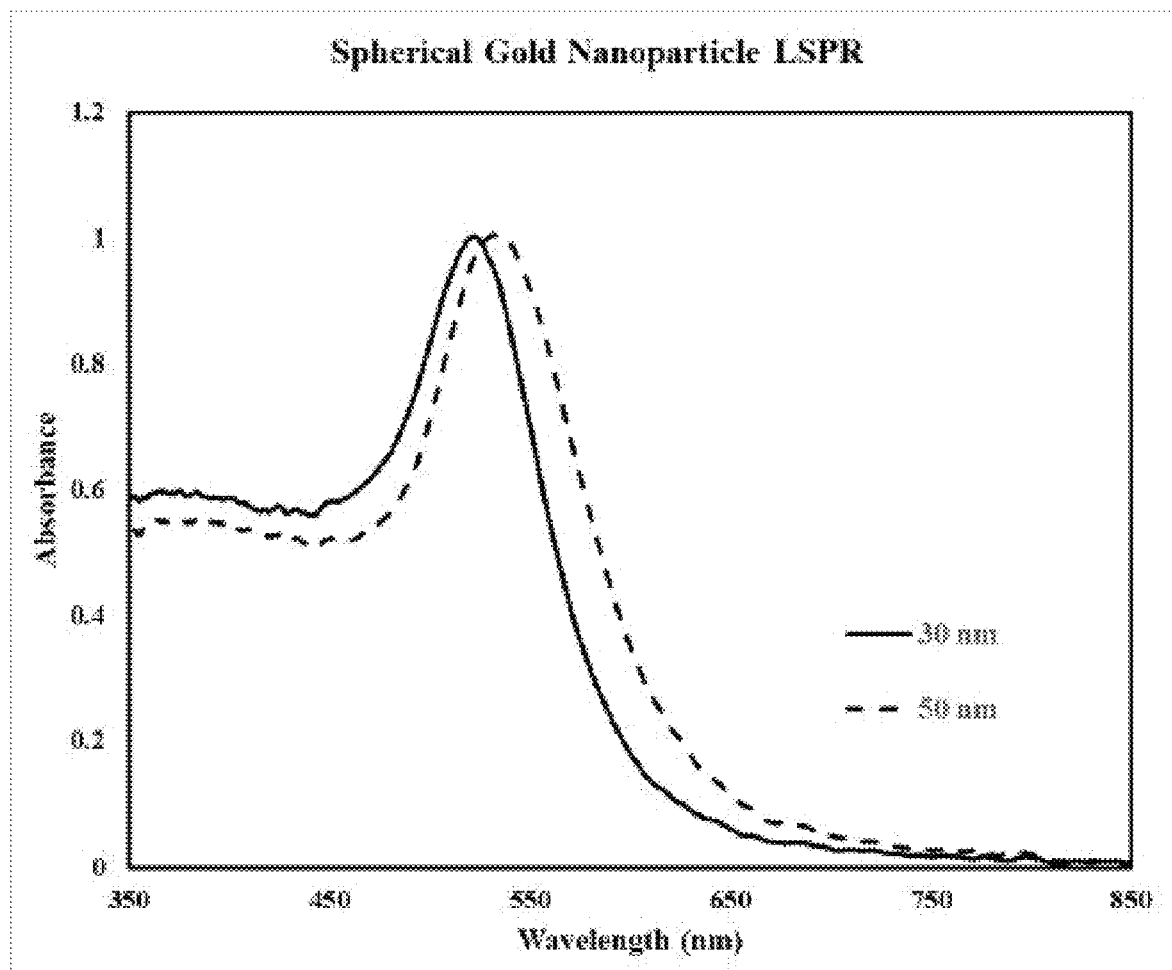
FIG. 12 shows the absorption spectrum of the as-synthesized spherical gold nanoparticle solution.

Colloidal suspensions of spherical gold nanoparticles (SGNs) were synthesized using a sodium citrate reduction method to form the aqueous nanoparticle phase. The resulting nanoparticles will be citrate capped particles stabilized in the aqueous solution. A 250 mL gold chloride solution (aq) was brought to a boil under vigorous stirring followed by a quick injection of microliter volume of sodium citrate solution. The mixture was allowed to continue boiling for 20 minutes and the final solution was placed in the fridge overnight before use. Particle size was controlled by the volume of the reducing agent administered to the gold salt solution during synthesis. As shown in FIG. 12, approximately 60 nm diameter (LSPR ~538 nm) particles were prepared according to aforementioned protocol, a size which allowed for efficient and controlled layer formation. A solution of NPs with smaller diameters were synthesized and tested for layer formation. Smaller particles (~30 nm, LSPR ~528 nm) formed fragile layers which took longer fabrication time to form and, in most cases, experienced surface cracks. The use of larger nanoparticles (>50 nm) was ruled out by the broad NP size distribution (broad LSPR peak), which would cause disorder and counter act the more controlled assembly of "like" particles.

Figure 13:
FIG. 13 shows NP Qualitative Characterization.

FIG. 12 shows the absorption spectrum of the as-synthesized spherical gold nanoparticle solution. One of the tested colloidal solutions presents an LSPR at approximate 528 nm which corresponds to an average particle diameter of approximate 30 nm. A decrease in the volume of sodium citrate solution was incorporated for the second nanoparticle solution producing an average NP diameter size and LSPR of approximate 60 nm and 538 nm, respectively. FIG. 13 shows NP qualitative characterization. A quick qualitative examination of the spherical NP solutions. Following the synthesis, the initial indication of the nanoparticle size regime is by eye. The larger of the NPs has a purple color, whereas the smaller NP regime has a redder color. In another embodiment, the current process steps are scaled up, and synthesis yields approximately 230 mL which can be doubled and result in a nanoparticle solution with the same absorption spectrum.

The chosen spherical nanoparticle solution (~60 nm diameter) was centrifuged down (4000 rpm, 25 min) to form a concentrate (2-3 mL) which was then diluted by half. The use of nanoparticle concentrates, instead of the more dilute as-synthesized solution, ensured there were a greater number of nanoparticles per unit volume to promote efficient self-assembly. Still, a diluted nanoparticle concentrate was necessary to reduce layer stacking and limit the assembly of nanoparticles into a 3D structure instead of a uniform layer, as shown in FIG. 13.

Figure 14:
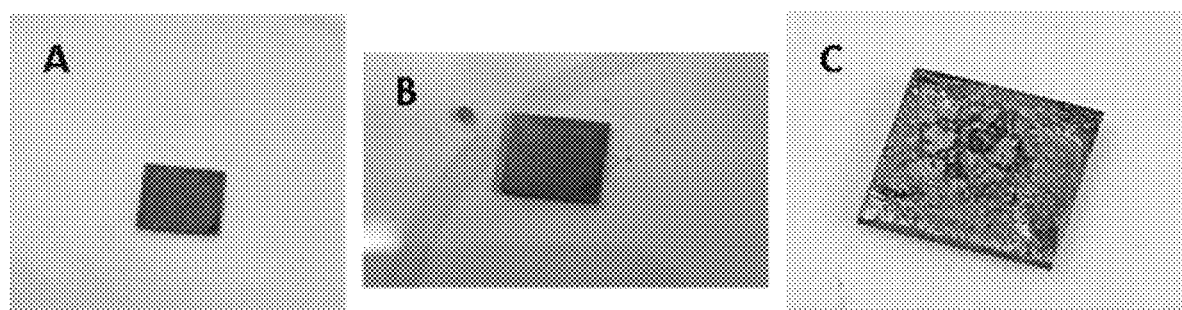
FIG. 14 shows examples of resulting NAAO substrates which had undergone coating with an undiluted concentrate solution.

FIG. 14 shows that the nanoparticle concentrate must be diluted by half. Examples of resulting NAAO substrates which had undergone coating with an undiluted concentrate solution are shown in FIG. 14. Each substrate exhibits signs of uncontrolled, multiple layer formation. The multilayer formation is clear in the alternating dark and light ring features where stacked layers are likely formed. Substrate B shows that like substrate A, the discoloration and dark spots are an indication of multilayer formation although it is less pronounced. The percentage of monolayer areas are expected to increase on B with respect to substrate A. Substrate C is an extreme case of multilayer stacking. In this case, the extent of layer stacking has created an uneven topology that can be seen clearly by eye.

Additionally, gold nanorods solutions were prepared using a seed-mediated method where a nanoparticle seed (~2 nm) serves as a nucleation center for axial growth. To prepare the gold seed solution, a 10 mL CTAB solution was prepared in a warm water bath (28° C.). Once the CTAB was dispersed and the solution turned clear, microliter volume of $HAuCl_4$ was added to the CTAB solution. Under vigorous stirring, microliter volume of ice cooled $NaBH_4$ was rapidly injected. The solution continued to stir at 28° C. for 5 minutes. The seed solution had to age for at least 1 hour before use. To prepare the nanorods, another 10 mL CTAB solution was placed in a 28° C. warm water bath and spun until the solution remained clear. Microliter volume of $HAuCl_4$ was then added to the spinning CTAB solution, followed by the addition of 50-100 µL $AgNO_3$ solution. After 1 minute, microliter volume of HCl was added. Vigorous stirring was applied to the solution before rapidly adding 80 µL of ascorbic acid. Lastly, microliter volume of the seed solution was added. The final nanorods solution was lightly stirred in the warm water bath for 30 minutes.

Unlike the spherical particles, the nanorods are passivated with a positively charged cetyltrimethyl ammonium bromide (CTAB) ligand which hinders the in-situ ligand exchange at the water/oil interface, a requirement for this assembly protocol. Layering using the current nanorods structures is unstable and requires additional ligand exchange process steps following synthesis and prior to concentrate formation, as shown in FIG. 15.

The volume of NP concentrate that was added to an individual substrate was determined for 4×4, 7×7, and 10×10 mm NAAOs. The starting concentrate volume depended on the size of the substrate in that an amount was chosen based on concentrate filling up the entire substrate.

Figure 15:
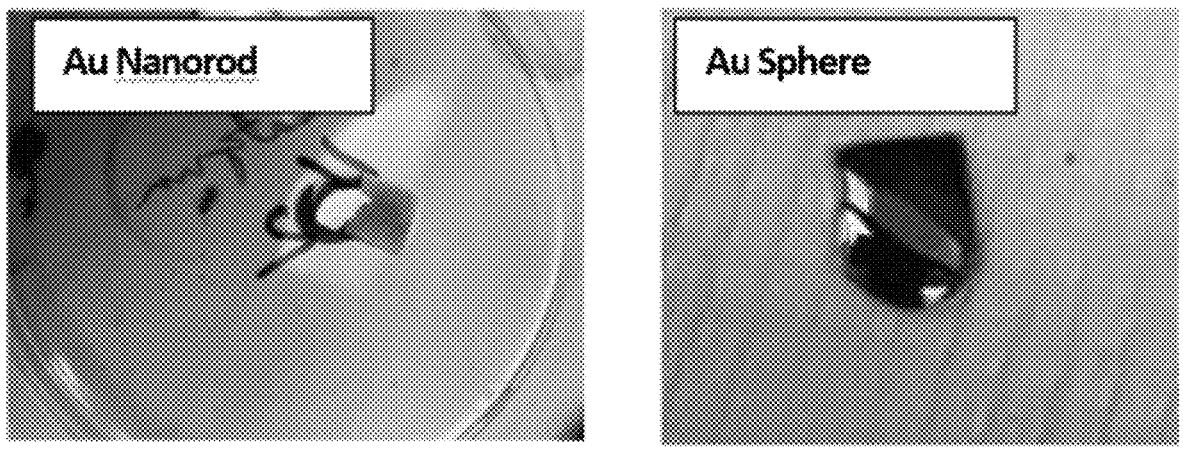
FIG. 15 shows unstable NR Layer.

FIG. 15 shows unstable NR layers. A gold nanorods layering was conducted under the same conditions as the spherical particles, but a stable well-adhered layer on top the NAAO doesn't form, as shown in the left panel. For CTAB-passivated NRs, self-assembly is slow and cracks form during solvent evaporation. This behavior was predicted to some extent when comparing the initial nanorods concentrate which was more dilute after centrifugation than the spherical concentrate, as shown in the right panel.

Key points for Aqueous Phase includes (1) approximately 60 nm spherical NPs required; (2) need to dilute NP concentrate to half for controlled layering; (3) unstable layering with CTAB-capped nanorods; (4) NRs will require ligand exchange prior to three-phase fabrication; (5) nanoparticle synthesis can be readily up scaled.

Organic (Oil) Phase: Alkylamine-Doped Hexane

The organic (oil) phase, doped with a long chain alkylamine, was prepared to create a water/oil interface for an in-situ ligand exchange and phase transfer. At the water/hexane interface, a ligand exchange takes place as the citrate ligands on the NPs are replaced by the alkylamine ligands. Dodecylamine (dd, $C12-NH_2$) was dispersed in the hexane (Hex) solvent to produce a solution which was $0.5 \times 10^{-6}$ M ddHex. This long chain amine has been shown to achieve efficient phase transfer when compared to shorter carbon chain amines. Ordered gold nanoparticle films have been successfully formed within a ddHex concentration range of $0-4.17 \times 10^{-4}$ M. Gold films with a greater ddHex concentration were also fabricated. Film formation proceeded faster using the greater concentrated ddHex, but the resulting film after drying was non uniform and resembled the substrates in FIG. 14, therefore unsuccessful.

One other long chain amine (an eighteen-carbon chain instead of twelve) was tested to assess any changes in the formation of the film and the resulting SERS sensing. An octadecylamine (od, $C18-NH_2$), hexane phase was prepared at the same concentration as the previous dd-Hex phase and tested for NP assembly. Assembly was successful and produced a similar layer to the ddHex-fabricated layer. Slight changes in the color (shifted LSPR wavelength) of the film were evident which was expected since the scattering wavelength depends strongly on the NP interparticle separation, which is controlled by the alkylamines. On average the band intensities did not vary from ddHex to odHex. Carbon chain length in the alkylamine is being further investigated in order to further optimize the carbon chain length in the gold layer which strongly depends on the structural properties of the nanoparticle.

Figure 16:
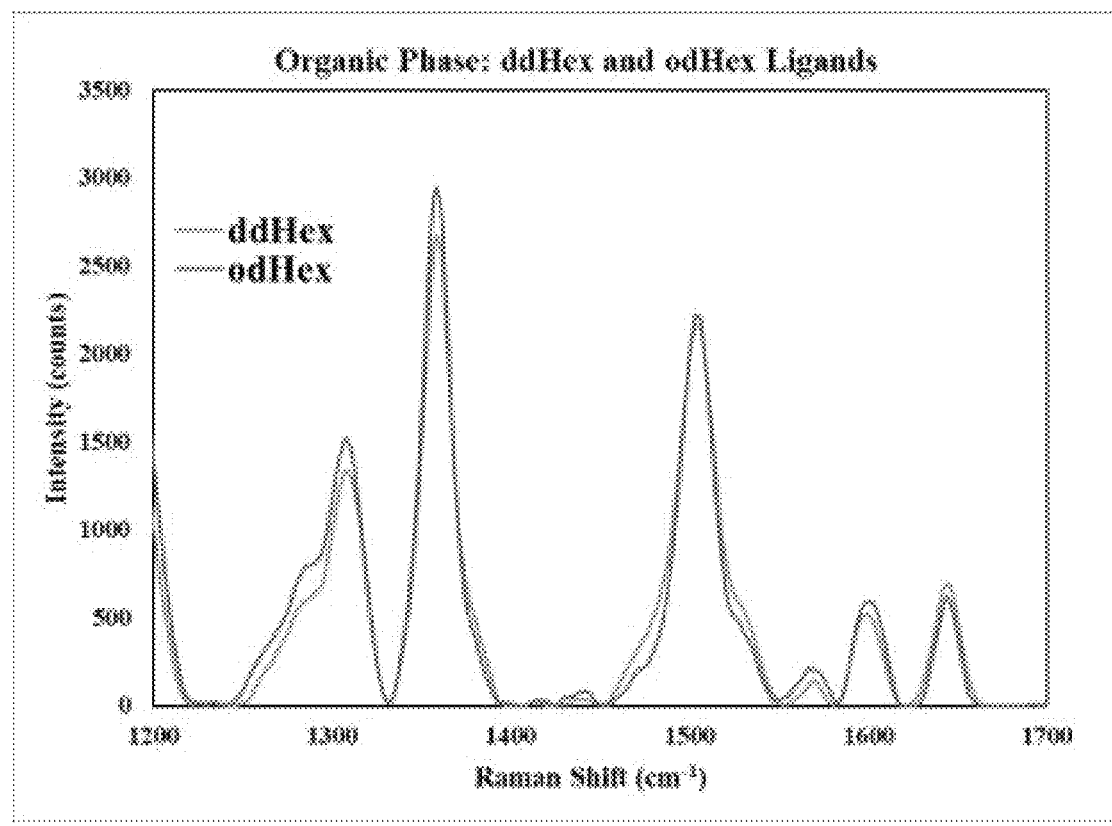
FIG. 16 shows ddHex vs odHex.

FIG. 16 shows ddHex vs odHex. The SERS spectrum for R6G loaded onto a SERS-NAAO fabricated using ddHex ($C^{12}$—$NH_2$) and one fabricated using odHex ($C^{18}$—$NH_2$). The SERS spectrum for R6G loaded onto each NAAO was collected and the two spectra share all the same bands, and the peak intensities were comparable for both systems. Although there was a shift in the optical properties of the resulting films, the R6G SERS signal for dd and od capped nanoparticles were very similar.

The volume of the organic layer necessary for successful gold layering is closely related to the volume of the assembly container. For the laser cut substrate sizes studied here, containers with a range of materials (polystyrene, glass) and volumes (4 mL-115 mL), have been tested for successful layering. These parameters have a great effect on the gold layering process because they determine the volume necessary to form three separate phases. Two different containers prove to be the best conditions for the current fabrication process. One container is a simple capped disposable petri dish with a max volume of 115 mL. The other container is a 4 mL capped glass vial. Both assembly container materials can be scaled to containers with a larger volume.

Lastly, another important impact to fabrication is the draining of the organic solution after the film has formed. The fabrication protocol described here results in two classes of SERS-NAAO. According to FIG. 14, its evident that allowing the organic solution to evaporate in a semi-controlled environment (closed petri dish) resulted in a shiny gold coat with few regions of discoloration (darker spots). When the organic solution is drained/siphoned off before placing the lid on the petri dish the coat consistently results in a darker matte coat which has obvious regions of discoloration. These two fabricated types of SERS-NAAOs are separated into classes due to their differing optical properties.

Figure 17:
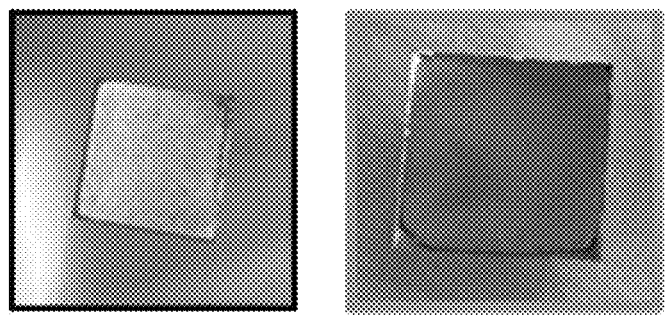
FIG. 17 shows the diagram of draining the organic layer.

FIG. 17 shows the diagram of draining the organic layer. The left panel shows Class 1 SERS-NAAO which sat in the shallow pool of organic with the lid closed while it dried; while the right panel shows Class 2 SERS-NAAO dried in a closed petri dish after the organic solution was removed after gold film was formed.

The key points for organic phase includes (1) 0.5×10-6 M dodecylamine in hexane (ddHex); (2) Continued work using long chain amines; (3) 2-5 mL of ddHex; (4) 10×10 mm substrates are processed in disposable petri dish; (5) 7×7 mm and 4×4 mm are processed in the 4 mL glass vial; (6) Container volume and material has the potential to be scaled up for larger production volumes.

Air Phase

Figure 18:
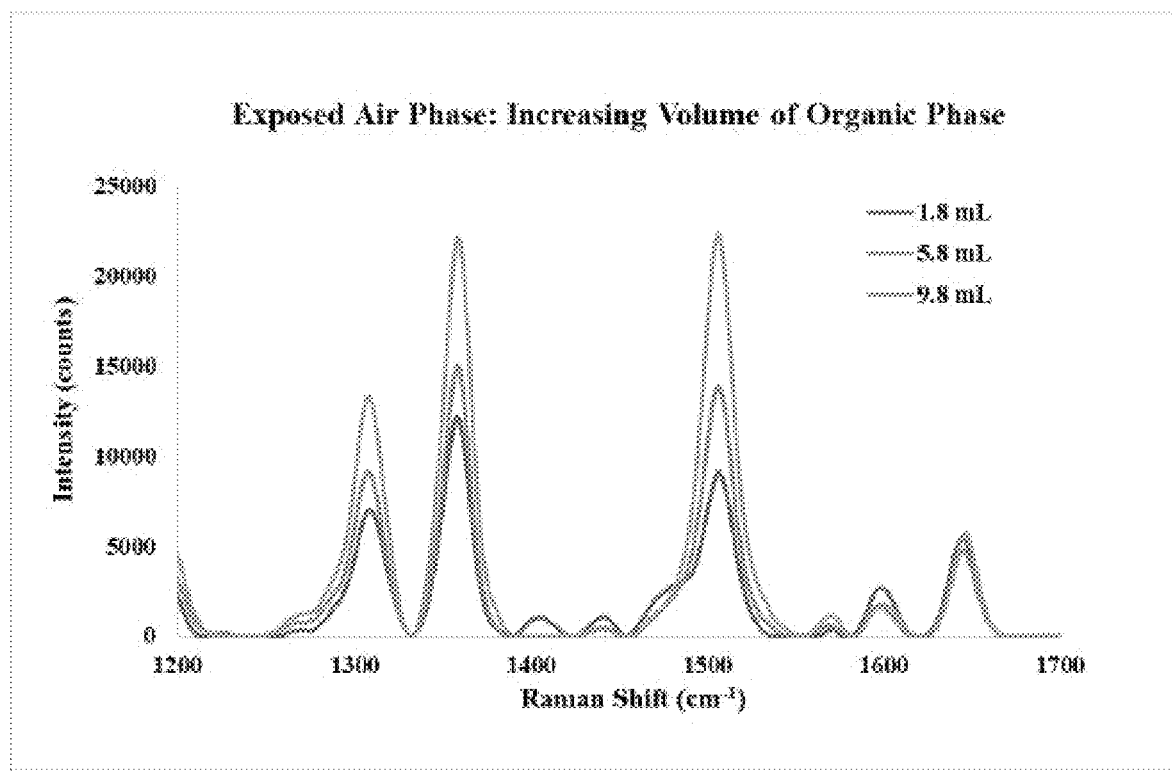
FIG. 18 shows exposed air phase.

As previously discussed, the area of air-exposed aqueous NP layer depends primarily on the volume of the assembly container and the volume of the organic solution. After depositing nanoparticle concentrate on the NAAO, the volume of the added organic solution determined the extent (height) to which the nanoparticle droplet is exposed to the air. Rising level of organic solution covered more of the nanoparticle droplet, therefore leaving a reduced area of air exposed NP surface. Experiments were carried out to adjust the size of the exposed droplet and measure the SERS signal for R6G on the resulting SERS-NAAO, as shown in FIG. 18. This area of development continues to be explored further to determine the optimum organic volume for the 115 mL petri dish and the 4 mL glass vial.

According to FIG. 18, substrates with the same dimensions were gold layered using an increasing amount of organic solution. An increasing organic volume on the same NP droplet volume reduced the amount of NP surface area which was exposed to air. The size of the exposed area directly affected the SERS signal for R6G, where a greater organic volume (smaller exposed area) provided the greatest enhancement.

During fabrication steps, the exposed air phase maintained a temperature around room temperature (23° C. in lab). Formation and drying in a colder environment like the fridge or freezer reduced the formation speed, increased the drying time, and ultimately resulted in an unimproved gold layer compared to room temperature conditions. Once removed from the cold environment, the nanoparticle concentrate droplet showed signs of still being wet and the dryer areas showed layer stacking.

Drying at room temperature overnight also required that the petri dish or vial be capped. Assembly containers which were left open during the drying process resulted in pronounced uneven drying of the gold layer. The gold layer could have been greatly influenced by environmental changes in the air (mechanical, thermal etc.) and further disturbed when drying.

The key points for Air Phase include (1) air phase should be close to room temperature for overnight drying; (2) important to control the volume of exposed liquid phase; (3) No drying in fridge to avoid multilayer stacking; (4) SERS signal strongly affected by the volume of droplet exposed to air; (5) Assembly containers must be closed during evaporation.

Chemical Inducer: Ethanol

The as-synthesized gold nanoparticles are stabilized in solution with the reducing agent citrate acting as the capping ligand. The citrate molecule creates a negatively charged nanoparticle surface which limits assembly due to interparticle electrostatic repulsion. The electrostatic interactions prevent the nanoparticles from aggregating, therefore keeping them suspended in solution. On the other hand, this electrostatic repulsion prevents the nanoparticles from forming closely packed arrays at the water/oil interface. For SERS sensing, the gold nanoparticles need to be tightly packed to form nanometer scaled interparticle gaps for EM field enhancement. For this fabrication process, it's essential that the electrostatic repulsion between nanoparticles be overcome to form a SERS-active 2D array. Here, interfacial self-assembly is induced with the careful addition of ethanol as a charge reduction method. The addition of ethanol destabilizes the nanoparticles which drives them to the water/hexane interface, where they undergo an in-situ ligand passivation with dodecylamine. The new ligand helps reduce the electrostatic repulsion, by controlling the interparticle separation between the nanoparticles, therefore causing the formation of gold layer.

Microliter volumes of ethanol were administered to the water/hexane interface using a sterile syringe at a rate of 1 drop per minute. Compared to a disposable glass pipette, the smaller syringe tip allowed for more precise drops that caused less movement when added. It was very important that the addition of ethanol did not disturb the nanoparticle droplet on the NAAO. The location of addition within the assembly container also had a great effect on the overall film. Ethanol addition was tested at several distances away for the substrate. These tests confirm an approximate optimum distance from the substrate for adding ethanol. When the syringe was placed almost touching the nanoparticle droplet, the gold layer was readily formed but the addition clearly caused a disturbance to the film. Spots on the film were darker than others due to the close-range disturbance caused by the ethanol. Ethanol drops were also administered closer to the edge of the container wall. This type of addition slowed down film formation, mainly because the ethanol in the ddHex fluid had to gradual flow to the substrate. Ultimately, an approximate distance of 0.2 inches from the edge of the square substrate was implemented. Ethanol addition at this distance away, but dropped near the square corner, was also used to reduce disturbance during layer formation. In the future for scaled-up fabrication, ethanol addition can be tested using a non-circular shaped nozzle.

The key points for the chemical inducer include (1) ethanol drives assembly acting as a charge reduction method; (2) the rate of addition has to be controlled, here 1 drop/minute; (3) a sterile syringe tip allowed addition of ethanol without disturbing droplet; (4) ethanol is administered 0.2 inches away for substrate edge.

SERS-NAAO Surface Optical Characterization: Reflectance Spectroscopy

Figure 19:
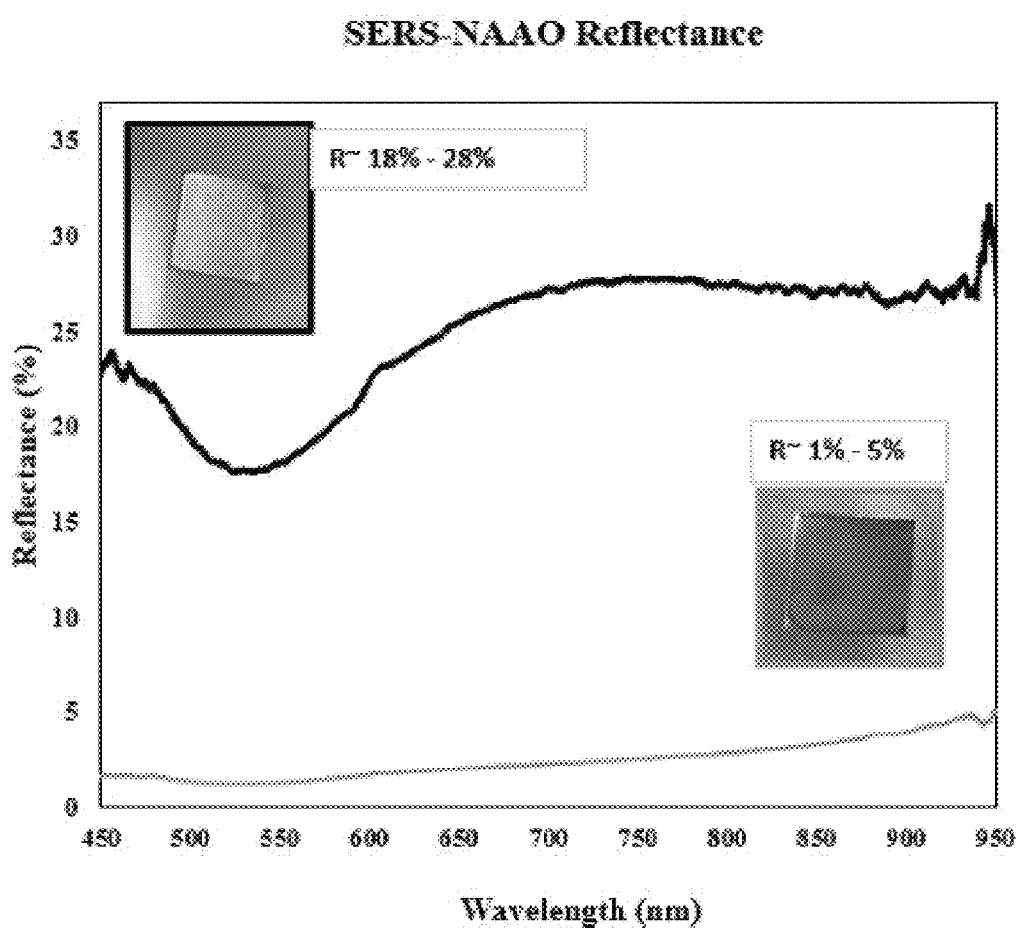
FIG. 19 shows Class 1 and Class 2 SERS-NAAO display characteristic reflectance features in the spectra.

Following fabrication, the dried SERS-NAAO sensors are optically characterized with UV-Vis reflectance spectroscopy, as shown in FIG. 19. The spectrum gives insight into the plasmonic coupling in the gold nanoparticle array and the optical response to the incident light when moving forward to laser induced excitation. The "dip" feature at ~530 nm is due to the surface plasmon absorption of the deposited gold nanoparticles. Another broad dip present in the NIR region results from the coupling of individual nanoparticles when forming the gold array in the layer. The alkylamine brings the nanoparticles within nanometers of each other, causing the surface plasmons of nearby particles to hybridize creating a low energy mode for NIR excitation.

Two classes of SERS-NAAO (10×10 mm) substrates were reproduced using the discussed protocol. Class 1 includes the SERS-NAAOs which remained in the shallow organic pool after the gold film formed and class 2 refers to substrates that once the gold film was formed an additional draining/siphoning step was implemented to remove the organic solution. After processing, the gold film is allowed to dry in the petri dish and covered with the lid. A closed drying environment was implemented to attempt to control the conditions of the air phase (e.g., mechanical, thermal). When the organic solution remains in the closed dish with the gold film during evaporation, this results in a Class 1 SERS-NAAO which is shinier and uniform after drying and has a reflectance percentage in the range 18%-28%. Gold films dried after removing the organic solution, Class 2, were darker in color and presented more regions of discoloration. The reflectance percentage for Class 2 SERS-NAAOs had reflectance percentages in the range of 1%-5%. The spectrum for each class showed the same features although the feature at ~530 nm was more pronounced for Class 1. Class 2 substrates are likely more absorptive for a range of reasons including the presence of larger aggregate structures that did not assemble into the ordered array. The greater extinction (absorption+scattering) properties observed for Class 2 substrates is negatively counteracted by a non-uniformity brought on most likely by the larger gold nanoparticle aggregates.

FIG. 19 shows Class 1 and Class 2 SERS-NAAO. Two classes of SERS-NAAOs were observed following fabrication and drying. Class 1 and class 2 display characteristic reflectance features in the spectra. The main differences being the increase in reflectance from 18% to 28% and pronounced LSPR dip at 530 nm for the class 1 SERS-NAAO.

Reflectance spectroscopy as a characterization method is a quick and simple method for checking the optical properties of the NAAO that result for the gold layering. The reflectance probe can be translated to measure the reflectance spectrum across a larger SERS-NAAO surface area. An error in the average reflectance percentage for the plasmonic spectral features can be determined and monitored for quality insight. For the current substrates, the error in reflectance percentage and error is 17±2% at 530 nm and 27±3% at 800 nm.

The key points of SERS-NAAO optical properties includes (1) LSPR modes in the visible and NIR; (2) coupled NIR band for 785 nm excitation; (3) two classes: Class 1 (no drain) Class 2 (organic drain); (4) reflectance percentage 18%-28%; and (5) reflectance spectrum good for quality determination.

SERS-NAAO Surface SERS Sensing of Phenylalanine in Water

Figure 20:
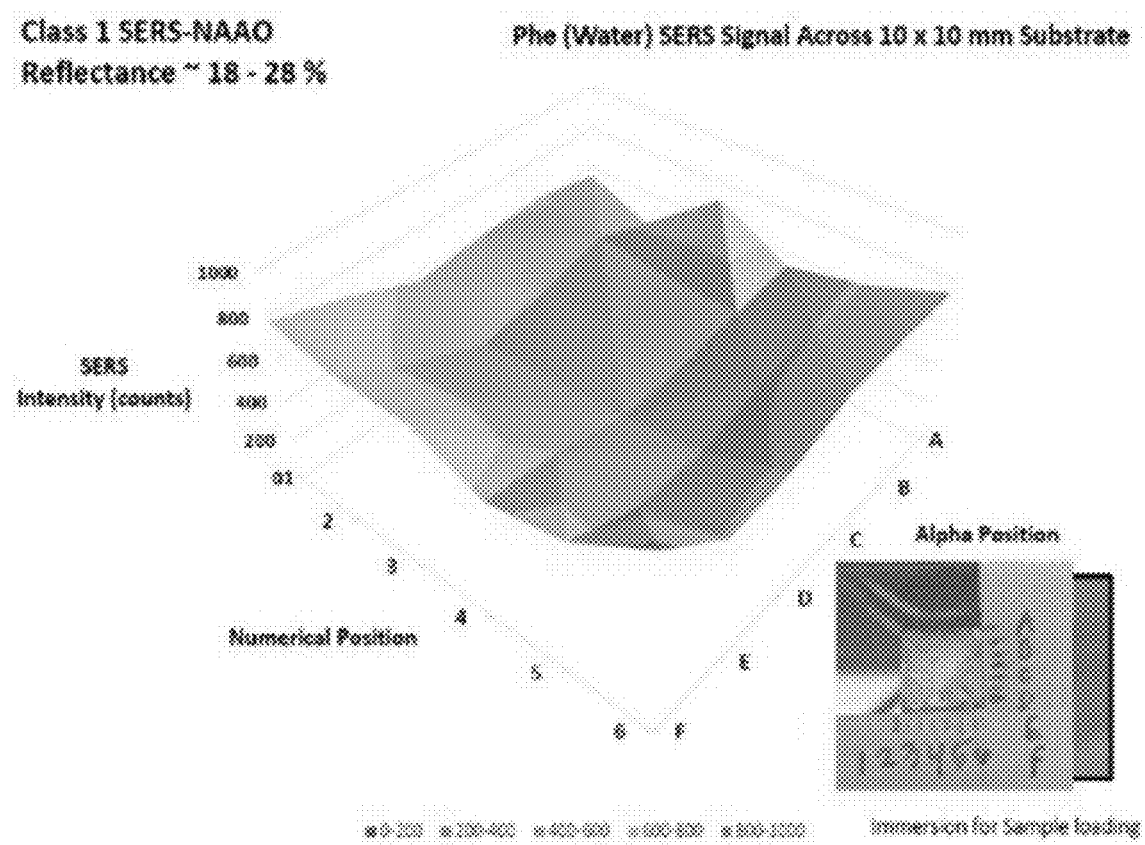
FIG. 20 shows uniformity of SERS Signal, Class 1 SERS signal collected at 36 points across the class 1 substrate.
Figure 21:
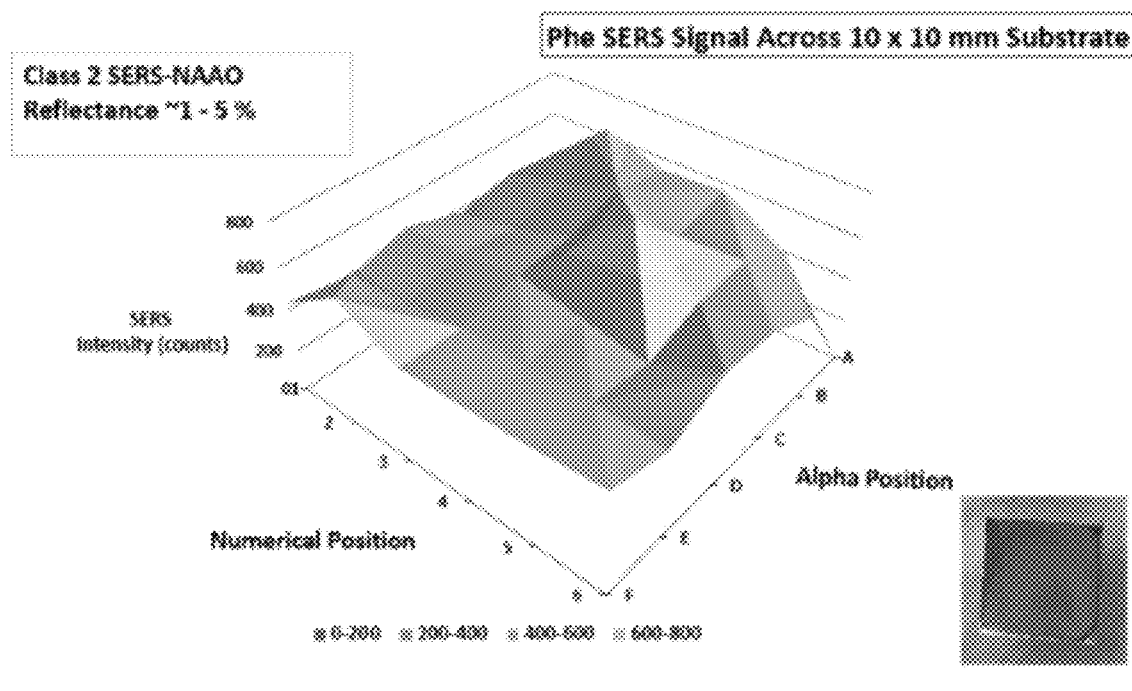
FIG. 21 shows uniformity of SERS Signal, Class 2 SERS signal collected at 36 points across the class 2 substrate.

The SERS spectra for phenylalanine in water loaded (by immersion) onto class 1 and class 2 SERS-NAAO substrates were collected following 785 nm excitation of the NIR plasmonic band. To gain insight into the uniformity of the three-phase gold layer, the 10×10 mm substrates were used for the SERS measurements to collect the phenylalanine signal at points across a large active area of the substrate. FIGS. 20-21 show the surface plot for the SERS signal at the Phe band (994 $cm^{-1}$) for 36 points across the class 1 and 2 substrates, respectively. The average intensity on the class 1 and class 2 substrates were 589 counts and 486 counts, respectively (grey regions). For the class 1 substrate, higher signal was detected at the outer perimeter of the substrate (yellow regions) which is likely due to non-uniform drying where nanoparticles flow to the edges upon evaporation. This has been described in the literature as the "coffee ring" effect (CRE) at the air/liquid interface that can be mitigated by controlling the particle-substrate, particle-flow, and particle-interface interactions. The class 2 substrate, as shown in FIG. 21, has a localized region with a greater than average intensity. This is due to the non-uniformity of the layer (darker spots) and potentially the sample immersion step.

The error of the SERS signal across the substrate also provides insight into the uniformity of the gold layer across the 10×10 mm substrate. For the class 1 and class 2 SERS-NAAO substrate the error is 18% and 22%, respectively, upon immersion in the sample solution. The errors are promising keeping in mind the wet-chemistry carried out to fabricate the surface and the uneven distribution of phenylalanine following immersion. Ultimately, the application will have a blood sample deposited on the substrate active area (both classes 10×10 mm active area) and localized in a μL droplet volume in the center. The size of the drop of blood for glucose measuring can range from 0.3 to 1 μL. In the blood studies to be discussed, 6 μL drop took up substantially less space in just the center of the substrate (grey region). Smaller substrate dimensions which are more proportional to the area taken up by the blood droplet should be considered.

FIG. 20 shows that Class 1 SERS signal collected at 36 points across the class 1 substrate. The laser excitation spot was translated across the substrate at these locations identified with alpha-numerical names. The substrate image is showing the SERS-NAAO following immersion. The substrate obtained some scratches during experimentation which will influence the signal counts and error. For signal collection the power was 6.3 mW, integration time 2 s, 3 averaged spectra, and 1 box smoothing correction.

FIG. 21 shows that Class 2 SERS signal collected at 36 points across the class 2 substrate. The substrate has dark regions that are caused by multilayers stacking. This stacking results in non-uniform layers that contribute to lowered reproducibility signal within a reasonable error. Even with contributions for the stacked regions, the error here is 22% which is also promising when compared to the shiny, uniform class 1 substrate which has an error of 18%. For signal collection, the power was 6.3 mW, integration time 2 s, 3 spectra average, and 1 box smoothing correction.

Figure 22:
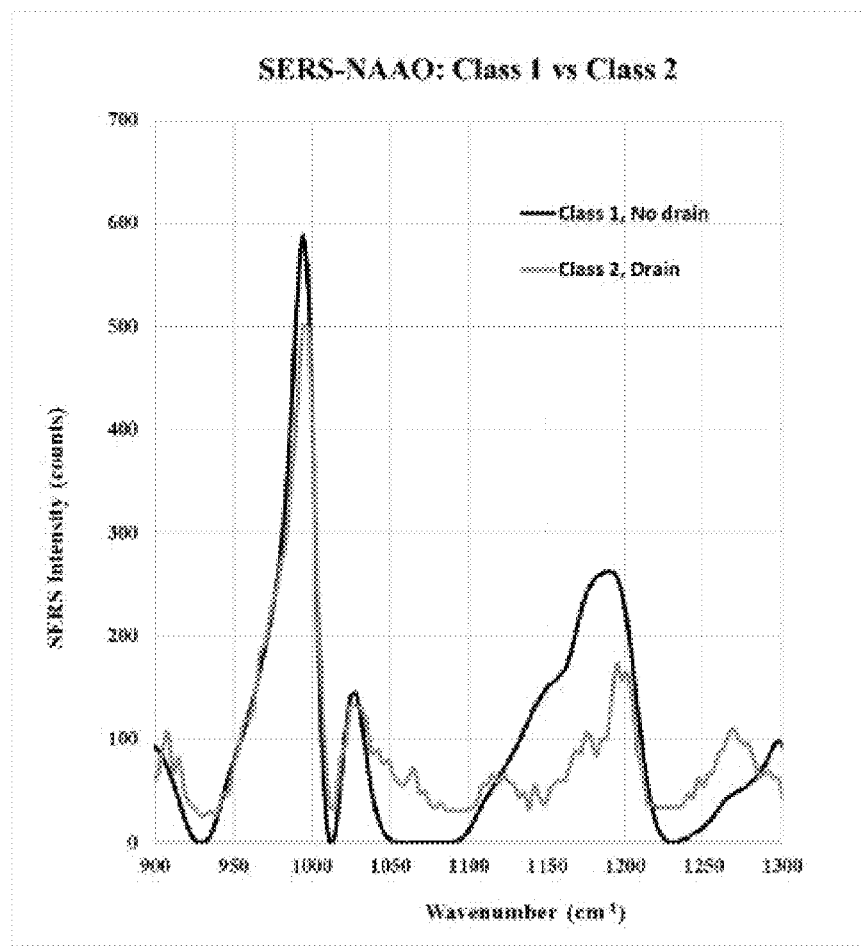
FIG. 22 shows averaged Phe (water) sensing behavior the SERS spectra for phenylalanine (water) adsorbed onto the class 1 and class 2 gold layers have a similar signal intensity, but the class 2 substrate provides a non-uniformity surface resulting in a noisy spectrum for some bands.

FIG. 22 displays the truncated SERS spectrum for phenylalanine (water), isolating two vibrational modes at 994 $cm^{-1}$ and 1194 $cm^{-1}$. The spectrum for each class is an average of the spectrum obtained at all 36 points to gain insight into overall SERS signal across the entire landscape of the gold layers. The spectra represent the signal achievable for the phenylalanine molecule loaded onto SERS-NAAOs with an approximate 20% error. The spectral differences in FIG. 22 between class 1 and class 2 are related to the optical properties of each substrate obtained in the reflectance, the uniformity of the self-assembled gold nanoparticles, and the successful adsorption of phenylalanine at the surface and interparticle gaps of the nanoporous gold film. The reflectance spectra indicated the self-assembly and coupling of adjacent nanoparticles in both films forming a LSPR mode in the visible and NIR. For SERS detection, this LSPR "dip" in the reflectance spectrum was pumped using 785 nm excitation resulting in an amplified Phe signal. The uniformity for the class 2 substrate is represented by a 22% error which could be the main contribution to the noisy signal in FIG. 22 (orange trace). The non-uniformity is apparent in the images of the class 2 substrate where uncontrolled nanoparticle assembly resulted in larger aggregate structures making Phe adsorption at some bonds problematic. Although, the error isn't substantially different between the two classes which is apparent in the similar band intensities. Moving forward with development of the SERS-NAAOs, the signal intensity and error determined here using our collection parameters will be used as a benchmark for further improvements to the gold layering protocol.

The key points of SERS Sensing Phenylalanine in water includes (1) Class 1 substrates had the highest signal intensity and lower signal error; (2) small substrate should be considered for application, smaller than 10×10 mm; (3) CFE has to mitigated to provide uniformity from the center to the edges of the substrate; and (4) a signal error of 22% for class 1 substrates will serve as benchmark.

SERS-NAAO Surface SERS Sensing of Phenylalanine in Whole Blood

Figure 23:
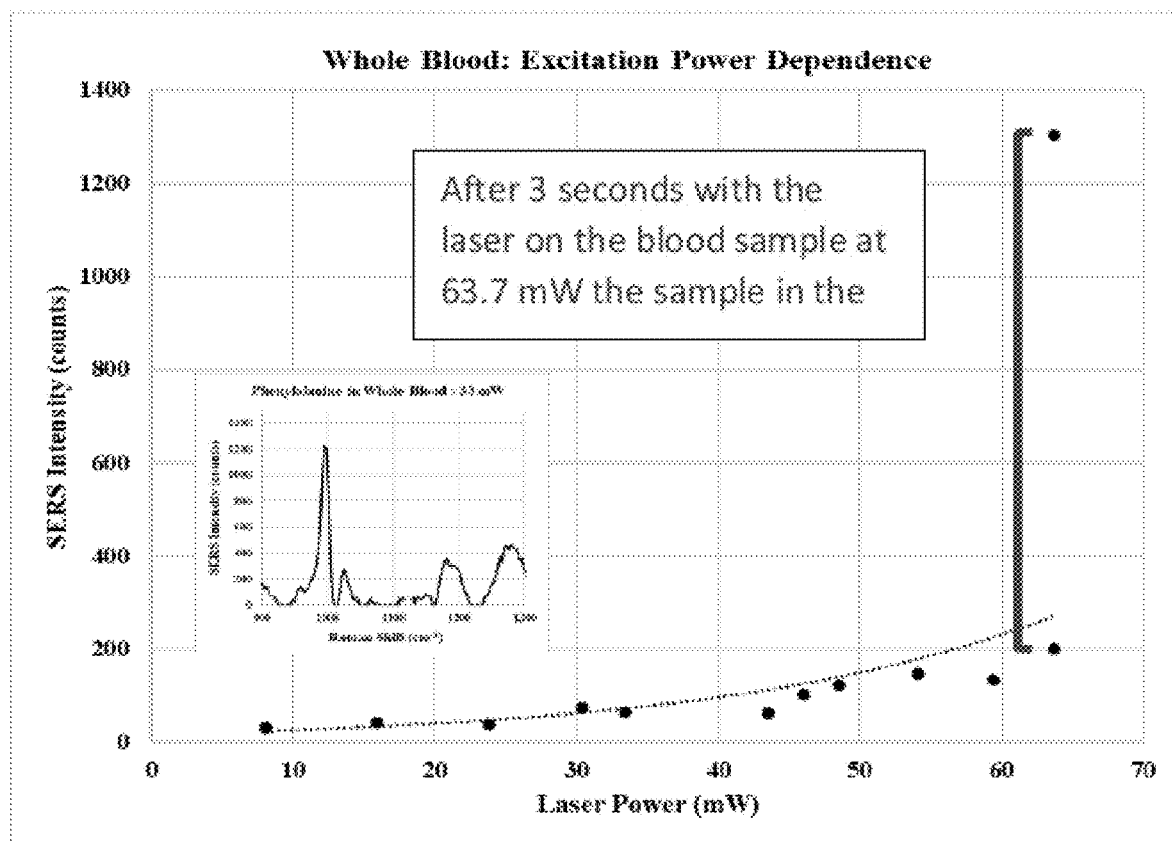
FIG. 23 shows the intensity of a blood component band at 752 cm$^{-1}$ as a function of power.

Prior to collecting the SERS spectrum for phenylalanine in whole blood, a power study of whole blood alone was conducted. Biological samples are broken down at moderate laser powers, therefore it's important to determine the power threshold when sensing in blood on the SERS-NAAOs. Fortunately, the aluminum-based substrate of the present invention is a mechanically and thermally robust surface, and not the limiting component to signal collection at higher laser powers, capable of tolerating powers above 100 mW. FIG. 23 shows the intensity of a blood component band at 752 $cm^{-1}$ as a function of power. When conducting the power study, leaving the laser impingent on the sample in between power changes resulted in breakdown in the blood at 45 mW. Removing the laser in between changing the powers and collecting fewer average spectra increased the breakdown threshold to 63.7 mW. At this high power, the spectra quickly evolves into a series of unresolved peaks that are likely not directly related to a specific vibration of phenylalanine, and the peak intensity nonlinearly increases from around 200 counts to 1300 counts. The SERS spectrum for phenylalanine in whole blood was collected at several incident laser powers. A power of 33 mW was the maximum power allowable before the phenylalanine doped sample began to degrade. In one embodiment, the SERS spectra in blood will be collected using a is integration time or lower and a power below 20 mW to be conservative and avoid damaging the sample during interrogation.

As shown in FIG. 23 with respect to power threshold of whole blood, SERS signal was collected for blood at a range of powers 8.1-63.7 mW. Using the current Raman system and a 3 s integration time, a power of 45 mW begins to destroy the sample, but lowering the integration time to 1 s allows for laser excitation to extend out to 60 mW. Also, reducing the number of averaged spectra during collection can also reduce the likelihood of damaging the components in the blood sample.

The key pointes of SERS sensing phenylalanine in whole blood includes (1) lower excitation powers are necessary for excitation in whole blood; (2) a resting laser on the substrate damages the sample at 45 mW; (3) removing the laser between collection increased sample damage threshold to 63.7 mW; (4) for phenylalanine in whole blood the highest power allowed for our system is 33 mW; and (5) future SERS measurements will be conducted at a power lower than 20 mW.

Figure 24:
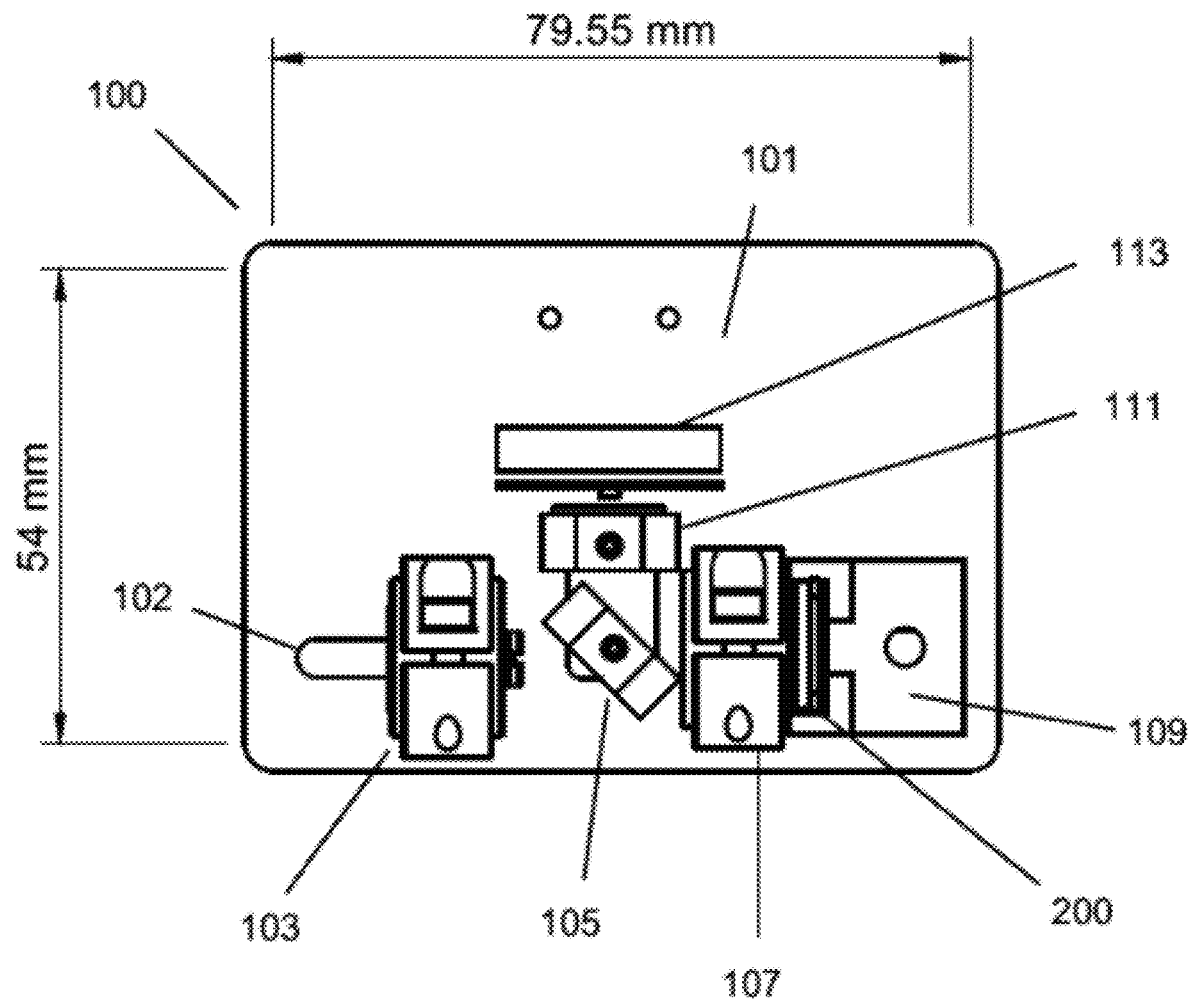
FIG. 24 shows a top schematic view of a handheld SERS device for detection of Phe in a PKU patient's blood.
Figure 25:
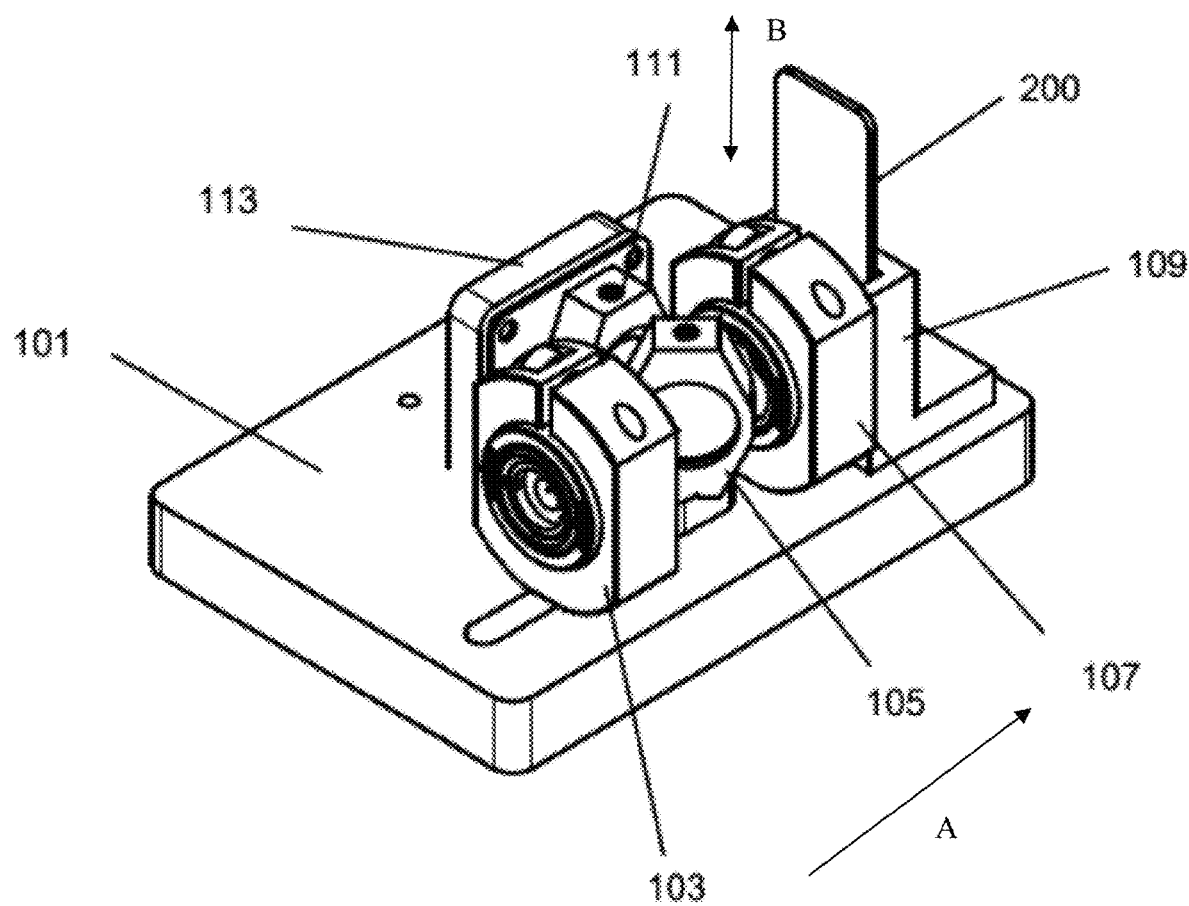
FIG. 25 shows a diagonal schematic view of the handheld SERS device for detection of Phe in a PKU patient's blood.
Figure 26:
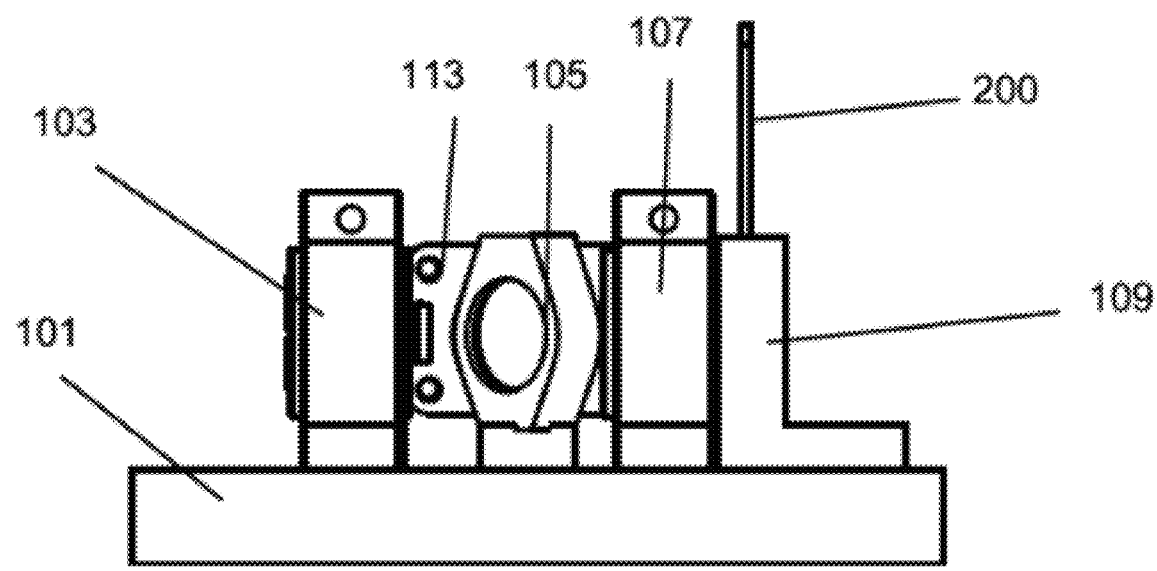
FIG. 26 shows a lateral schematic view of the handheld SERS device for detection of Phe in a PKU patient's blood.
Figure 27:
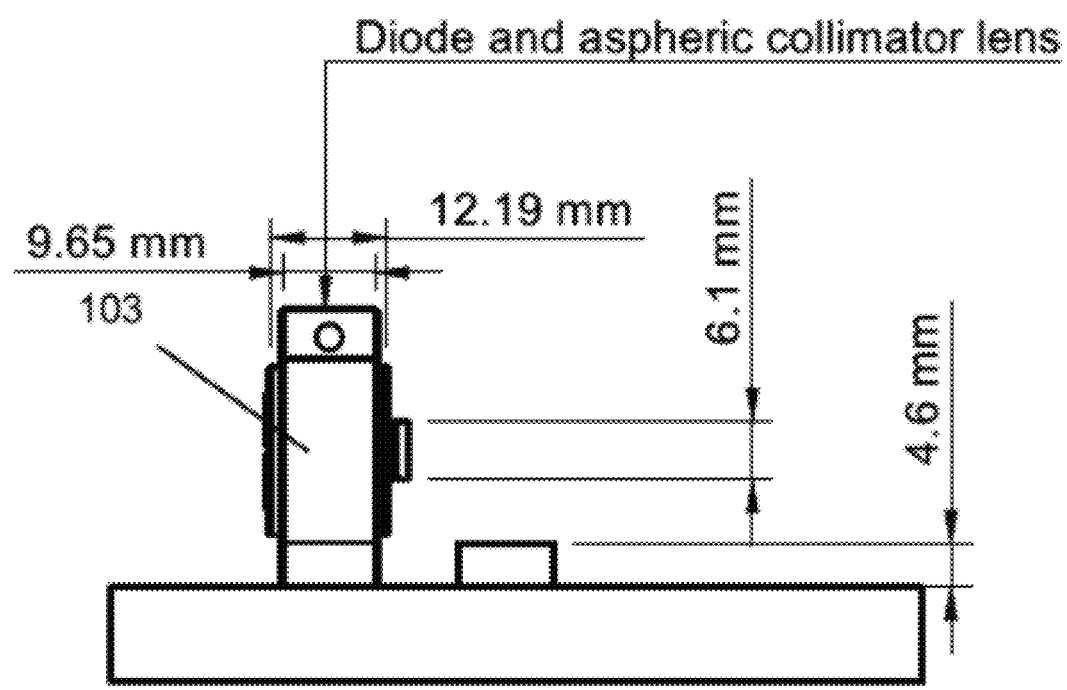
FIG. 27 shows a lateral schematic view of the diode and aspheric collimator lens mounted on the base of the handheld SERS device.
Figure 28:
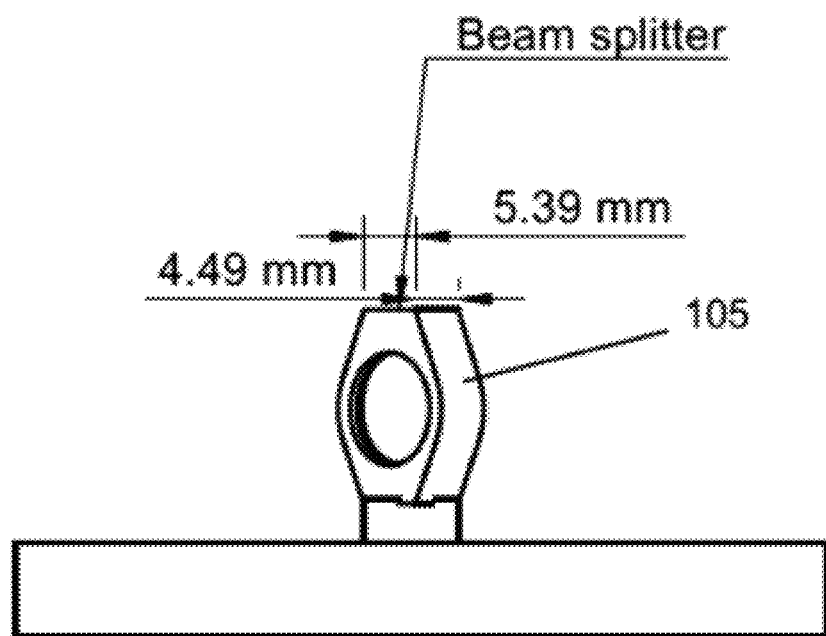
FIG. 28 shows a lateral schematic view of the beam splitter mounted on the base of the handheld SERS device.
Figure 29:
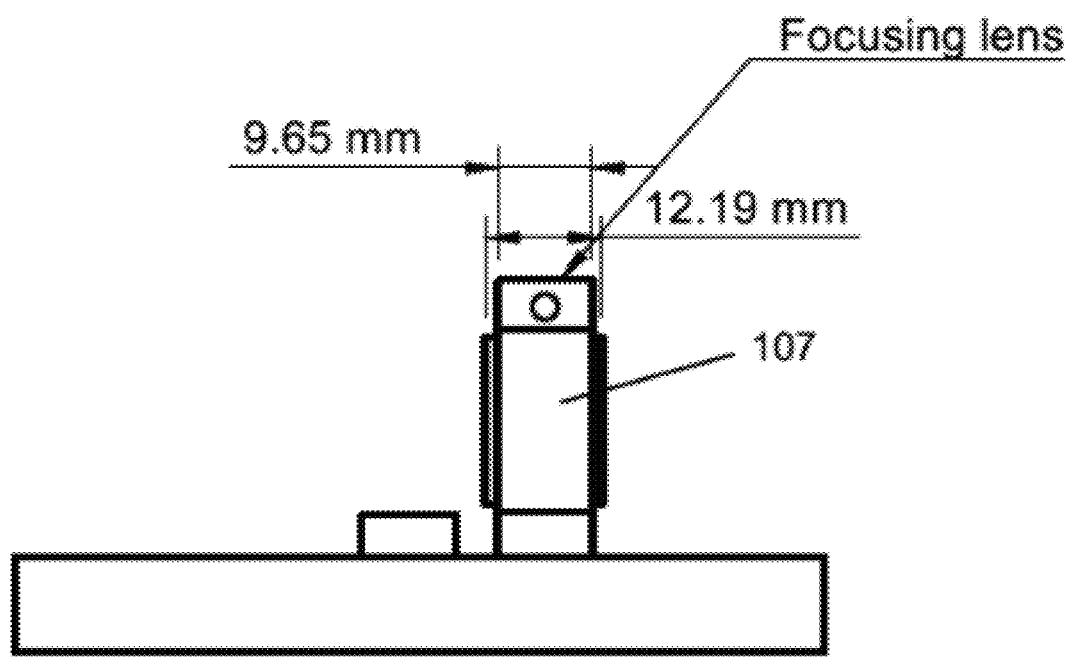
FIG. 29 shows a lateral schematic view of the focusing lens mounted on the base of the handheld SERS device.
Figure 30:
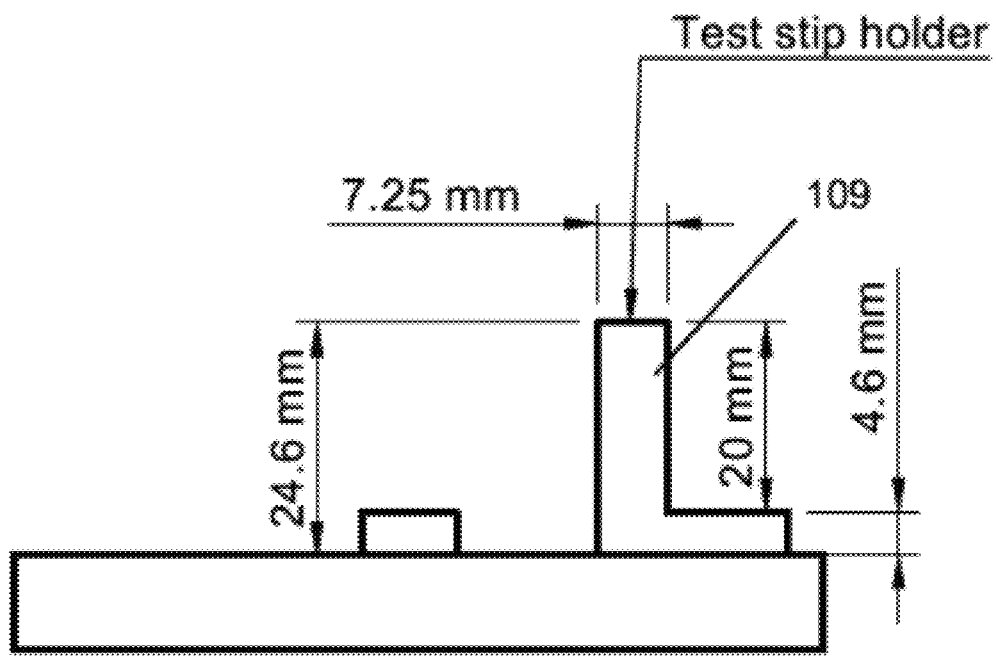
FIG. 30 shows a lateral schematic view of the test strip holder mounted on the base of the handheld SERS device.
Figure 31:
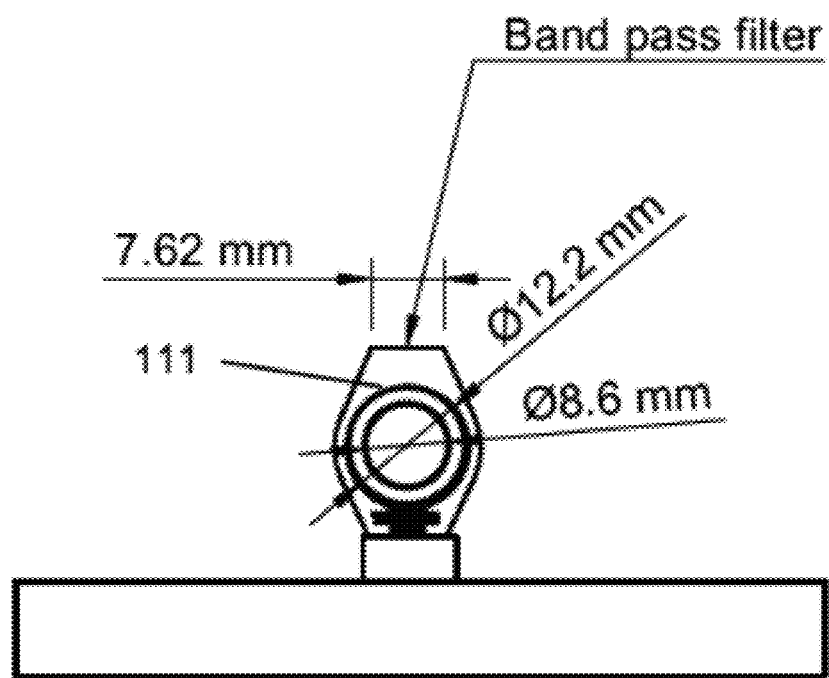
FIG. 31 shows a lateral schematic view of the band pass filter mounted on the base of the handheld SERS device.

SERS Handheld Device for Detection of Phe in PKU Patient's Blood and NAAO Test Strip Used in Association with the SERS Handheld Device FIGS. 24-26 show the schematic views of the SERS handheld device 100. In particular, the SERS handheld device 100 comprises a base 101 which has an approximately handheld size. In one embodiment, the base 101 has a length of about 50 mm, 60 mm, 70 mm, 80 mm, 90 mm, 100 mm, 150 mm, 200 mm, and 250 mm. In one embodiment, the base has a width of about 20 mm, 30 mm, 40 mm, 50 mm, 60 mm, 70 mm, 80 mm, 90 mm, 100 mm, 150 mm, 200 mm, and 250 mm. A diode mount and aspheric collimator lens 103 are mounted on a top surface of the base 101 through proper fastening means, e.g. screw, nail, glue, welding, and etc. The diode mount may receive a laser generator 102, e.g. a diode, such that the laser generator provides a laser beam.

A beam splitter 105 is mounted to the top surface of the base 101 via proper fastening means. The beam splitter 105 is positioned to receive the laser beam on one of its sides, permitting the received laser beam from the laser generator 102 passing through it to reach a focusing lens 107 and a test trip 200 received in a test strip holder 109. The focusing lens 107 and test strip holder 109 are mounted to the top surface of the base 101 via proper fastening means. In one embodiment, the diode mount and aspheric collimator lens 103, the beam splitter 105, the focusing lens 107 and the test strip holder 109 are arranged in one straight line.

The laser beam reaches the test strip 200 and being reflected and/or deflected, passing through the focusing lenses 107 and reaches the other side of the beam splitter 105. The beam splitter 105 receives the reflected/deflected light and reflects the light to reach a band pass filter 111, which is mounted to the top surface of the base 101. In one embodiment, the band pass filter 111 selectively permits light of certain wavelength to pass through it so as to reach a light sensor 113 mounted on the base 101. In one embodiment, the beam splitter 105, the band pass filter 111 and the light sensor 113 are arranged in one straight line.

In one embodiment, the beam splitter 105 is arranged approximately 45 degree diagonally, relative to the straight line formed by the diode mount and aspheric collimator lens 103, the beam splitter 105, the focusing lens 107 and the test strip holder 109. In one embodiment, the beam splitter 105 is arranged approximately 45 degree diagonally, relative to the straight line formed by the band pass filter 111 and the light sensor 113. In another embodiment, this degree may be adjusted according to the size of the base, so as to provide optimal size of the handheld SERS device.

In one embodiment, the bandpass filter 111 will only allow photons at one vibrational energy (potentially a group of wavelengths) to reach the light sensor 113.

In one embodiment, the laser generator is a laser diode which is highly divergent, so the aspheric lens is necessary to collimate the laser light without introducing spherical aberrations. The collimated laser beam passes through the dichroic beam splitter 105 before becoming incident on the SERS-NAAO substrate on the test strip 200.

FIG. 25 shows the laser beam direction by arrow A, and directions for installing and removing of the test strop holder 109 is shown by double heads arrow B. In one embodiment, the test strip holder 109 is 3D printed piece which allows the dimensions to be matched to test strip. A port size in the housing can be adapted for test strip slot. In one embodiment, the test strip holder 109 is designed for the test strip 200. Once inserted, the test strip 200 remains fixed for excitation and signal collection.

In one embodiment, the bandpass filter 111 is tailored to exclusively transmit the phenylalanine signal to the detector. The center wavelength of the filter is controlled by tuning the angle of incidence. For collimated input light, independently rotating the bandpass filters serves to smoothly tune the combined transmission spectrum to the energy of the phenylalanine signal. Two filters define the short- and long-wavelength edges of the overall transmission curve.

FIGS. 27-31 show the individual elements, including the diode mount and aspheric collimator lens 103, the beam splitter 105, the focusing lens 107, the test strip holder 109, the band pass filter 111 and the light sensor 113, each being mounted to the base 101, and relative size of each element.

Figure 32A:
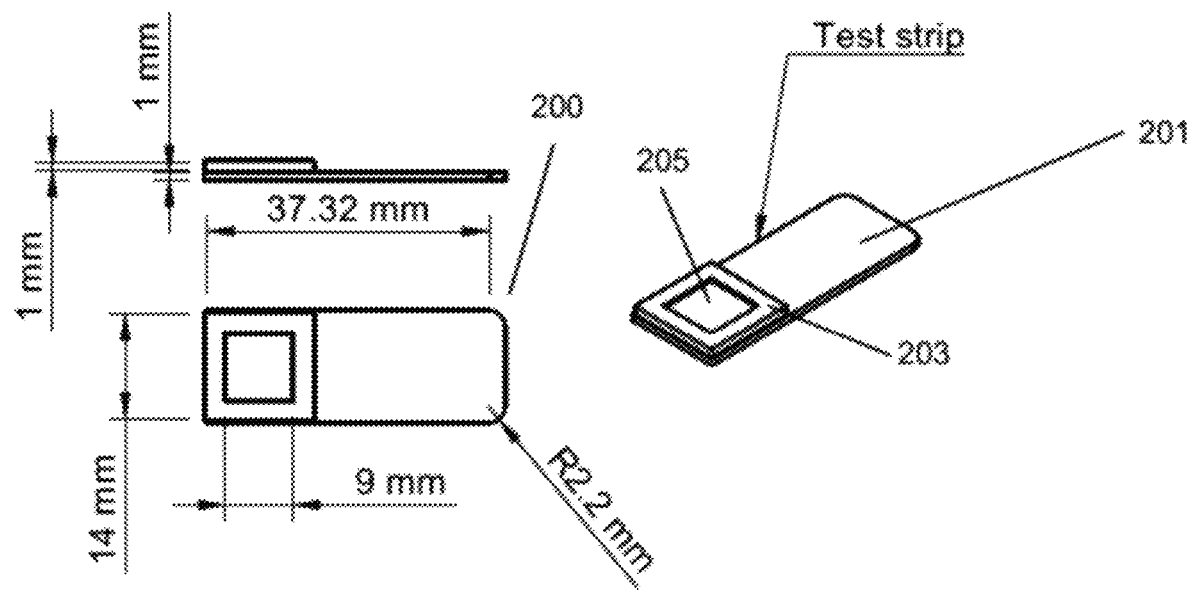
FIG. 32A shows schematic views of one embodiment of the test strip used in association with the handheld SERS device.
Figure 32B:
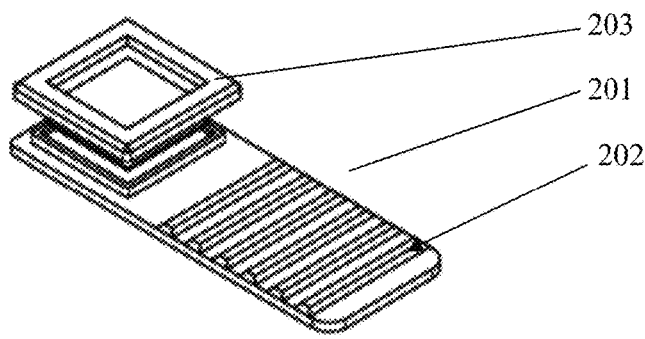
FIG. 32B shows schematic views of another embodiment of the test strip used in association with the handheld SERS device.
Figure 32B:

FIG. 32A shows one embodiment of the test strip 200. The test strip 200 includes a strip holder 201, a sample receiving substrate 205, and a sample rim 203 surrounding the sample receiving substrate 205. In one embodiment, the sample receiving substrate 205 includes the NAAO substrate fabricated according to at least one method disclosed above. In one embodiment, the test strip 200 has a thickness of less than 5 mm, 2 mm, 1 mm. In one embodiment, the sample receiving surface 205 and the rim 203 has a thickness of less than 1.5 mm, 1 mm, and 0.5 mm. FIG. 32B shows another embodiment of the test strip 200. In this embodiment, the strip holder 201 has rigged grooves 202 formed on top surface of the strip holder 201, so as to provide friction for a user of the device to hold the test strip 200 tight. The sample receiving substrate 205 has a gold layer 2051, a NAAO substrate 2052, and an aluminum layer 2053. In one embodiment, the gold layer 2051 is on top of the NAAO substrate 2052, which is on top of the aluminum layer 2053.

The test strip 200 receives a patient's test sample on its sample receiving surface. In one embodiment, the test sample contains a patient's blood. The test strip 200 is configured to be mechanically received by the test strip holder 109 of the SERS handheld device.

Figure 33:
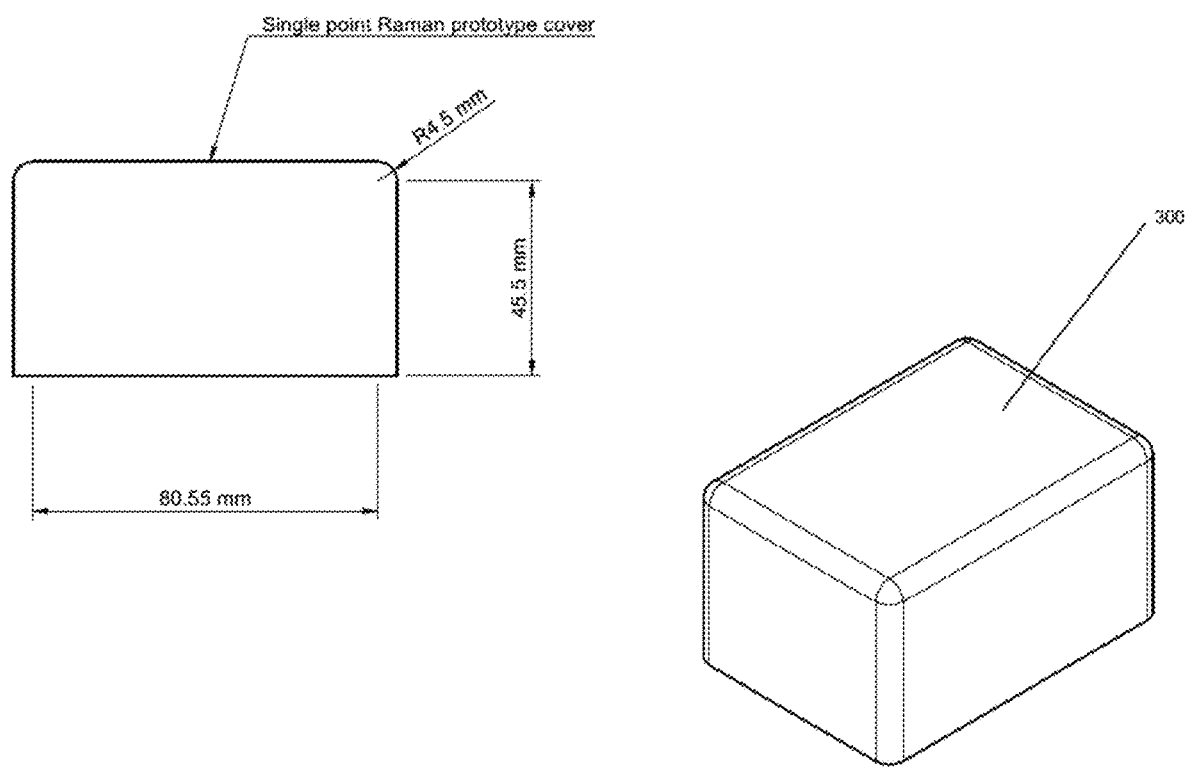
FIG. 33 shows a schematic view of a cover for the handheld SERS device.

FIG. 33 shows one embodiment of a cover 300 covering the SERS handheld device. The cover 300 and the base 101 form a housing enclosing the diode mount and aspheric collimator lens 103, the beam splitter 105, the focusing lens 107, the test strip holder 109, the band pass filter 111 and the light sensor 113. In one embodiment, the cover 300 is light-tight such that no laser beams would escape from, and no light would enter into the housing formed by the cover 300 and the base 101. The cover is built by additive manufacturing method. Cover is manufactured with durable material to protect laser, optics and detector. In one embodiment, a 3D printer is used to create the cover 300.

Figure 34:
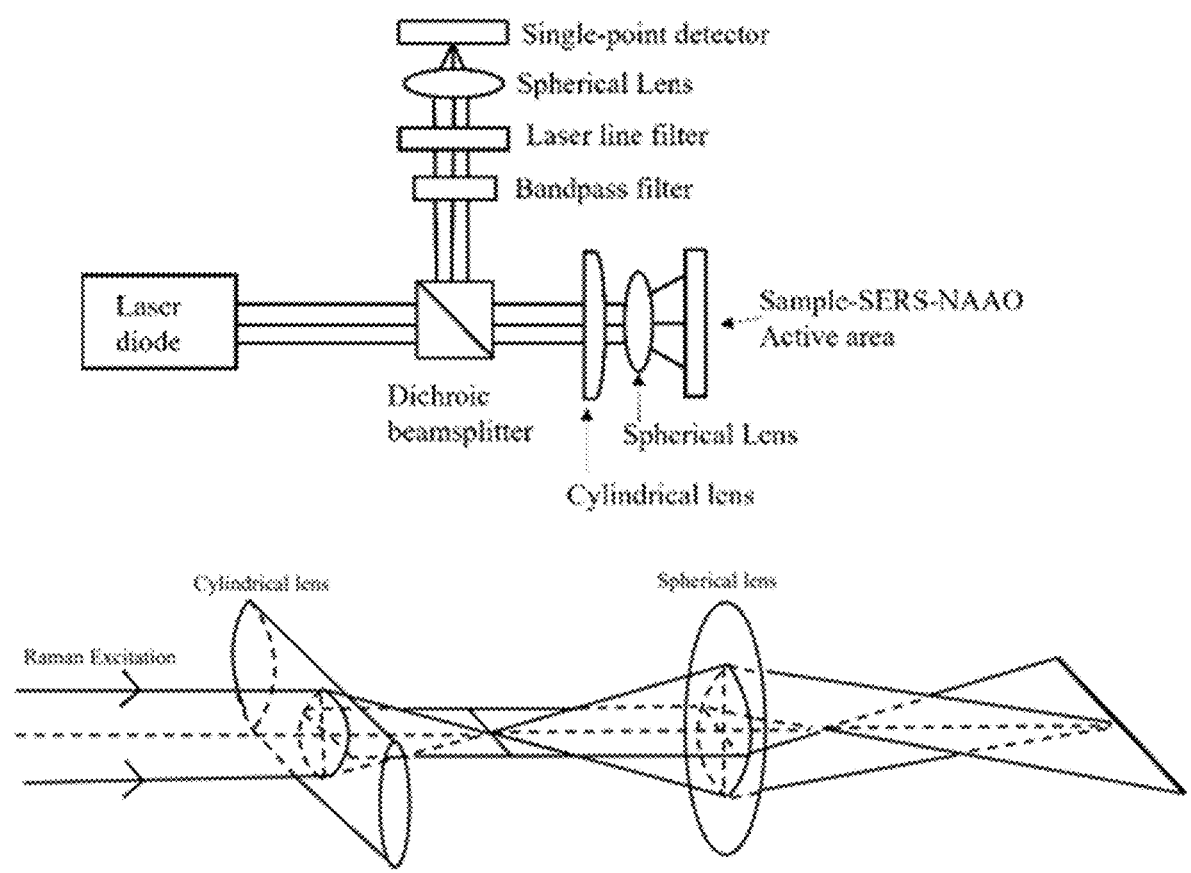
FIG. 34 shows another embodiment of spectrometer optical schematic in the upper panel and cylindrical lens for line focusing in the lower panel.

FIG. 34 shows another embodiment of spectrometer optical schematic in the upper panel and cylindrical lens for line focusing on the lower panel. Absorption of the focused laser light at the blood sample-SERS-NAAO can lead to local heating and photo induced processes at the blood sample-SERS-NAAO. To avoid this problem without enlisting a raster scanning system, a cylindrical lens can be introduced to the optical pathway. Use of the cylindrical lens changes the illuminated area of the sample so that a line-focus is met, such that a maximum amount of scattered light using reduced laser irradiation.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

REFERENCE LIST

Huang, Kai & Li, Yangjuan Wu, Zhiming & Li, Cheng & Lai, Hongkai & Kang, Junyong. (2011). Asymmetric light reflectance effect in AAO on glass. Optics express. 19. 1301-9. 10.1364/OE.19.001301.

Dengfeng Kuang, Renée Charrière, Natalia Matsapey, Manuel Flury, Jenny Faucheu, and Pierre Chavel, "Modeling the specular spectral reflectance of partially ordered alumina nanopores on an aluminum substrate," Opt. Express 23, 4506-4516 (2015)

M. Meinke, G. Muller, J. Helfmann, and M. Friebel, "Optical properties of platelets and blood plasma and their influence of the optical behavior of whole blood in the visible and near infrared wavelength range," J. Biomed. Opt., 12 014024 (2007).

Yang, Guang & Hallinan Jr, Daniel. (2016). Gold Nanoparticle Monolayers from Sequential Interfacial Ligand Exchange and Migration in a Three-Phase System. Scientific Reports. 6.35339. 10.1038/srep35339.

Park, Yong-Kyun & Yoo, Sang-Hoon & Park, Sungho. (2007). Assembly of Highly Ordered Nanoparticle Monolayers at a Water/Hexane Interface. Langmuir: the ACS journal of surfaces and colloids. 23. 10505-10. 10.1021/la701445a.

Ye, Ziwei & Li, Chunchun & Chen, Qinglu & Xu, Yikai & Bell, Steven. (2021). Self-Assembly of Colloidal Nanoparticles into 2D Arrays at Water-Oil Interfaces: Rational Construction of Stable SERS Substrates with Accessible Enhancing Surfaces and Tailored Plasmonic Response. Nanoscale. 13. 10.1039/D0NR08803J.

Yang, Guang & Chang, Wen-Sheng & Hallinan Jr, Daniel. (2015). A convenient phase transfer protocol to functionalize gold nanoparticles with short alkylamine ligands. Journal of colloid and interface science. 460. 164-172. 10.1016/j.jcis.2015.08.054.

Reincke, Francois & Hickey, Stephen & Kegel, Willem & Vanmaekelbergh, Daniel. (2004). Spontaneous Assembly of a Monolayer of Charged Gold Nanocrystals at the Water/Oil Interface. Angewandte Chemie (International ed. in English). 43. 458-62. 10.1002/anie.200352339.

Yang, Guang & Hallinan Jr, Daniel. (2016). Self-assembly of large-scale crack-free gold nanoparticle films using a 'drain-to-deposit' strategy. Nanotechnology. 27. 225604. 10.1088/0957-4484/27/22/225604.

Rohiman, Asep & Anshori, Isa & Surawijaya, Akhmadi & Idris, Irman. (2011). Study of Colloidal Gold Synthesis Using Turkevich Method. AIP Conference Proceedings. 1415. 39-42. 10.1063/1.3667215.

Mehtala, Jonathan & Zemlyanov, Dmitry & Max, Joann & Naveen, Kadasala & Zhao, Shou & Wei, Alexander. (2014). Citrate-Stabilized Gold Nanorods. Langmuir: the ACS journal of surfaces and colloids. 30. 10.1021/la5029542.

Wang, Maggie & Hoff, Alexandra & Doebler, Joseph & Emory, Steven & Bao, Ying. (2019). Dumbbell-Like Silica Coated Gold Nanorods and Their Plasmonic Properties. Langmuir. 10.1021/acs.langmuir.9b03133.14

Saute, Benjamin & Premasiri, Ranjith & Ziegler, L. & Narayanan, Radha. (2012). Gold Nanorods as Surface Enhanced Raman Spectroscopy Substrates for Sensitive and Selective Detection of Ultra-Low Levels of Dithiocarbamate Pesticides. The Analyst. 137. 5082-7.10.1039/c2an36047k.

Md Shah, Nur & Razali, Nur & Nafisah, Suratun & Morsin, Marlia & Sanudin, Rahmat & Salleh, Muhammad. (2018). Investigation on the Effect of Centrifugation Speed on the Shape Separation of Gold Nanorods. International Journal of Engineering and Technology. 7. 330-333.

Feng, Lili & Xuan, Zhenwen & Ma, Jiebing & Chen, Jun & Cui, Daxiang & su, Changwei &

Guo, Junming & Zhang, Yingjie. (2013). Preparation of gold nanorods with different aspect ratio and the optical response to solution refractive index. Journal of Experimental Nanoscience. 10. 258-267. 10.1080/17458080.2013.824619.

Al-Milaji, Karam & Zhao, Hong. (2019). New Perspective of Mitigating Coffee-Ring Effect: Interfacial Assembly. The Journal of Physical Chemistry C. 123. 10.1021/acs.jpcc.9b00797.

Yi, Johan & Jeong, Hwapyeong & Park, Jaesung. (2018). Modulation of nanoparticle separation by initial contact angle in coffee ring effect. Micro and Nano Systems Letters. 6. 10.1186/s40486-018-0079-9.

Yang, Guang & Hallinan Jr, Daniel. (2016). Self-assembly of large-scale crack-free gold nanoparticle films using a 'drain-to-deposit' strategy. Nanotechnology. 27. 225604. 10.1088/0957-4484/27/22/225604.

What is claimed is:

1. A gold nanoporous anodic aluminum oxide (NAAO) substrate used in coordination with a handheld Surface-Enhanced Raman Spectroscopy (SERS) device for detecting phenylalanine (Phe) in a sample collected from a subject, the gold NAAO substrate comprising:
a multilayered nanoporous aluminum layer; and
a gold layer disposed on top of the multilayered nanoporous aluminum layer,
wherein the gold layer comprises gold nanoparticles;
wherein the gold NAAO substrate is configured to receive the sample; and
wherein the gold NAAO substrate and the device detect the Phe in the sample.

2. The gold NAAO substrate according to claim 1, wherein
the multilayered nanoporous aluminum layer comprises an aluminum layer base, and a nanoporous alumina layer grown on top of the aluminum layer base.

3. The gold NAAO substrate according to claim 2, wherein the nanoporous alumina layer comprises a plurality of reflective alumina nanocavities.

4. The gold NAAO substrate according to claim 1, wherein the gold nanoparticles are nanorods.

5. The gold NAAO substrate according to claim 1, wherein the gold nanoparticles are nanospheres.

6. The gold NAAO substrate according to claim 1, wherein the gold NAAO substrate has a high surface area to volume ratio.

7. The gold NAAO substrate according to claim 1, wherein the gold nanoparticles are disposed onto the multilayered nanoporous aluminum layer via a wet chemical approach.

8. The gold NAAO substrate according to claim 7, wherein the wet chemical approach comprises injecting a cosolvent solution into a three-phase system.

9. The gold NAAO substrate according to claim 8, wherein the three-phase system comprises air/water/hexane interfaces.

10. The gold NAAO substrate according to claim 8, wherein the cosolvent solution comprises ethanol.

11. The gold NAAO substrate according to claim 9, wherein the cosolvent solution is injected into the water/hexane interface of the three-phase system.

12. The gold NAAO substrate according to claim 1, wherein the gold layer is a monolayer.

13. The gold NAAO substrate according to claim 1, wherein the gold NAAO substrate is detachable from the device.

14. The gold NAAO substrate according to claim 1, wherein the gold NAAO substrate is configured to receive a laser beam produced by a laser generator of the device.

15. The gold NAAO substrate according to claim 14, wherein the laser beam reaches the sample on the gold NAAO substrate and is reflected or deflected to produce a light signal; and a light sensor of the device is configured to receive the light signal reflected or deflected from the sample.

16. The gold NAAO substrate according to claim 1, wherein the gold NAAO substrate is disposed on a test strip.

17. The gold NAAO substrate according to claim 16, wherein the test strip is detachably received in a test strip holder of the device.

* * * * *